US010513702B2

(12) United States Patent
Kennedy et al.

(10) Patent No.: US 10,513,702 B2
(45) Date of Patent: Dec. 24, 2019

(54) SYNTHETIC HAMMERHEAD RIBOZYMES WITH LIGAND-RESPONSIVE TERTIARY INTERACTIONS

(71) Applicant: The Board of Trustees of the Leland Stanford Junior University, Stanford, CA (US)

(72) Inventors: Andrew Bodnar Kennedy, Sunnyvale, CA (US); Christina D. Smolke, Menlo Park, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 9 days.

(21) Appl. No.: 15/737,687

(22) PCT Filed: Jun. 17, 2016

(86) PCT No.: PCT/US2016/038214
§ 371 (c)(1),
(2) Date: Dec. 18, 2017

(87) PCT Pub. No.: WO2017/003726
PCT Pub. Date: Jan. 5, 2017

(65) Prior Publication Data
US 2018/0187192 A1    Jul. 5, 2018

Related U.S. Application Data

(60) Provisional application No. 62/186,767, filed on Jun. 30, 2015.

(51) Int. Cl.
*A61K 48/00* (2006.01)
*C07H 21/04* (2006.01)
*C12N 15/113* (2010.01)
*C12N 15/115* (2010.01)
*C12N 15/63* (2006.01)
*C12N 15/11* (2006.01)

(52) U.S. Cl.
CPC .......... *C12N 15/113* (2013.01); *C12N 15/111* (2013.01); *C12N 15/115* (2013.01); *C12N 15/63* (2013.01); *C12N 2310/121* (2013.01); *C12N 2310/16* (2013.01); *C12N 2310/3519* (2013.01); *C12N 2310/531* (2013.01); *C12N 2330/31* (2013.01)

(58) Field of Classification Search
CPC .......... C12Q 2521/337; A61K 2300/00; A61K 31/713; A61K 45/06
See application file for complete search history.

(56) References Cited

PUBLICATIONS

Auslander et al., "A general design strategy for protein-responsive riboswitches in mammalian cells", Nature Methods, Advance Online Publication, 2014, pp. 1-7.
Beisel et al., "Design Principles for Riboswitch Function", PLoS Computational Biology, 2009, 5(4):e1000363, pp. 1-14.
Hammann et al., "The ubiquitous hammerhead ribozyme", RNA, 2012, 18:871-885.
Kennedy et al., "Protein-responsive ribozyme switches in eukaryotic cells", Nucleic Acids Research, 2014, 42(19):12306-12321, doi:10.1093/nar/gku875.
Kennedy et al., "A versatile cis-blocking and trans-activation strategy for ribozyme characterization", Nucleic Acids Research, 2013, 41(2): e41, 13 pages, doi: 10.1093/nar/gks1036.
Liang et al., "A high-throughput, quantitative cell-based screen for efficient tailoring of RNA device activity", Nucleic Acids Research, 2012, 40(20): e154, 14 pages, doi:10.1093/nar/gks636.
Win et al., "A modular and extensible RNA-based gene-regulatory platform for engineering cellular function", PNAS, 2007, 104(36):14283-14288.

*Primary Examiner* — Amy H Bowman
(74) *Attorney, Agent, or Firm* — James S. Keddie; Bozicevic, Field & Francis LLP

(57) ABSTRACT

A ligand-responsive hammerhead ribozyme is provided. In some embodiments, the ribozyme comprises: i. a first loop that has been replaced by an RNA aptamer that binds to a ligand; and ii. a second loop comprising a modified sequence, wherein the aptamer and the second loop interact in a ligand-dependent manner and autocatalytic cleavage of the ribozyme is ligand-responsive.

20 Claims, 11 Drawing Sheets
Specification includes a Sequence Listing.

SYNTHETIC HAMMERHEAD RIBOZYMES WITH LIGAND-RESPONSIVE TERTIARY INTERACTIONS

CROSS REFERENCE TO RELATED APPLICATION

This application is a § 371 national phase of International Application No. PCT/US2016/038214, filed on Jun. 17, 2016, which claims priority benefit of U.S. Provisional Patent Application Ser. No. 62/186,767, filed on Jun. 30, 2015, which applications are incorporated by reference herein.

GOVERNMENT RIGHTS

This invention was made with Government support under grant no. HR0011-11-2-0002 awarded by the Defense Advanced Research Projects Agency (DARPA) and grant number GM086663 awarded by the National Institutes of Health (NIH). The Government has certain rights in the invention.

BACKGROUND

Engineered biological systems hold potential in programming cell behavior to advance sustainable technologies, materials synthesis, and human health. However, incomplete understanding of the sequence-structure-function relationships that govern the design space limits our capacity to access, process, and act on information in living systems. Methods for assessing sequence-structure-function landscapes and developing conditional gene-regulatory devices are thus critical to advancing our ability to manipulate and interface with biology.

Programmable RNA-based gene-regulatory devices comprise parts that encode sensing, information transmitting, and actuating functions. RNA device architectures connect sensor and actuator components, such that sensor-detected information is transmitted into controlled activity of the actuator. One class of RNA devices utilizes a hammerhead ribozyme (HHRz) actuator to modulate the stability of a target transcript through conditional control of cleavage activity via binding of the cognate ligand. The ribozyme-based device framework supports genetic controllers in different organisms, responsive to diverse ligands, exhibiting complex computation, and applied to regulate complex phenotypes. Sensor and actuator components are linked through a rationally designed or screened transmitter that guides secondary structure changes in the components. As RNA folding is largely hierarchical and dictated by localized hydrogen bonding and base stacking, secondary structure changes are tractable. While this approach enables sequence-level modular device design, it limits regulatory potential. The relatively slow kinetics associated with the transmitter-induced secondary structure rearrangement places a limit on self-cleavage kinetics, over which a trade-off between gene-silencing activity and ligand sensitivity is observed. To address performance limitations inherent with secondary structure switching RNA devices, a new device architecture that achieves faster switching is needed.

High-throughput in vitro and in vivo selection and screening strategies for creating RNA devices have been described. In vitro selections have largely been supplanted by cell-based (in vivo) strategies to avoid any change in activities when transitioning from in vitro to in vivo environments. In vivo strategies link device activity to a readily measureable expression output, such as fluorescence, motility, or viability. These strategies only reveal sequence-activity information on a small number of individually-tested sequences. Strategies that provide sequence-activity information for all members in large libraries are needed to rapidly identify all high-functioning RNA devices and gain a complete understanding of the sequence-structure-function landscape to enable more robust design strategies. Methods that integrate fluorescence activated cell sorting (FACS) and high-throughput next generation sequencing (NGS) have been applied to investigate and/or develop gene-regulatory elements such as translation initiation sites, N-terminal codons, and various cis-regulatory elements.

SUMMARY

Described herein is a ligand-responsive synthetic hammerhead ribozyme comprising: i. a first loop that has been replaced by an RNA aptamer; and ii. a second loop comprising a modified sequence, wherein the aptamer and the second loop interact in a ligand-dependent manner and autocatalytic cleavage of the ribozyme is ligand-responsive.

The architecture of the present ligand-responsive ribozyme forgoes strict sequence modularity and displays design-level modularity, where the sequence of the actuator changes with the sensor. This present ligand-responsive ribozyme is believed to show improved performance in terms of basal level, activation ratio, and ligand sensitivity as compared to the highest activity secondary-structure switching RNA devices described to date.

Also described is a reliable closed-end screening method for building high dynamic range ligand-responsive synthetic hammerhead ribozymes starting from preexisting aptamers based on a FACS/NGS approach (FACS-Seq) and statistical data analyses that enables parallel measurements of the activities of hundreds of thousands of sequences from device libraries. Through our massively parallel characterization method consensus sequences are determined that enable ligand-responsive tertiary interactions for each aptamer-integrated device. This method greatly increases the capacity to rapidly and reliably build genetic tools and provides insight into the sequence-structure-function relationships needed to guide rational design.

BRIEF DESCRIPTION OF THE FIGURES

The patent or application file contains at least one drawing executed in color. Copies of this patent or patent application publication with color drawing(s) will be provided by the Office upon request and payment of the necessary fee.

The skilled artisan will understand that the drawings, described below, are for illustration purposes only. The drawings are not intended to limit the scope of the present teachings in any way.

DEFINITIONS

Figure 1:
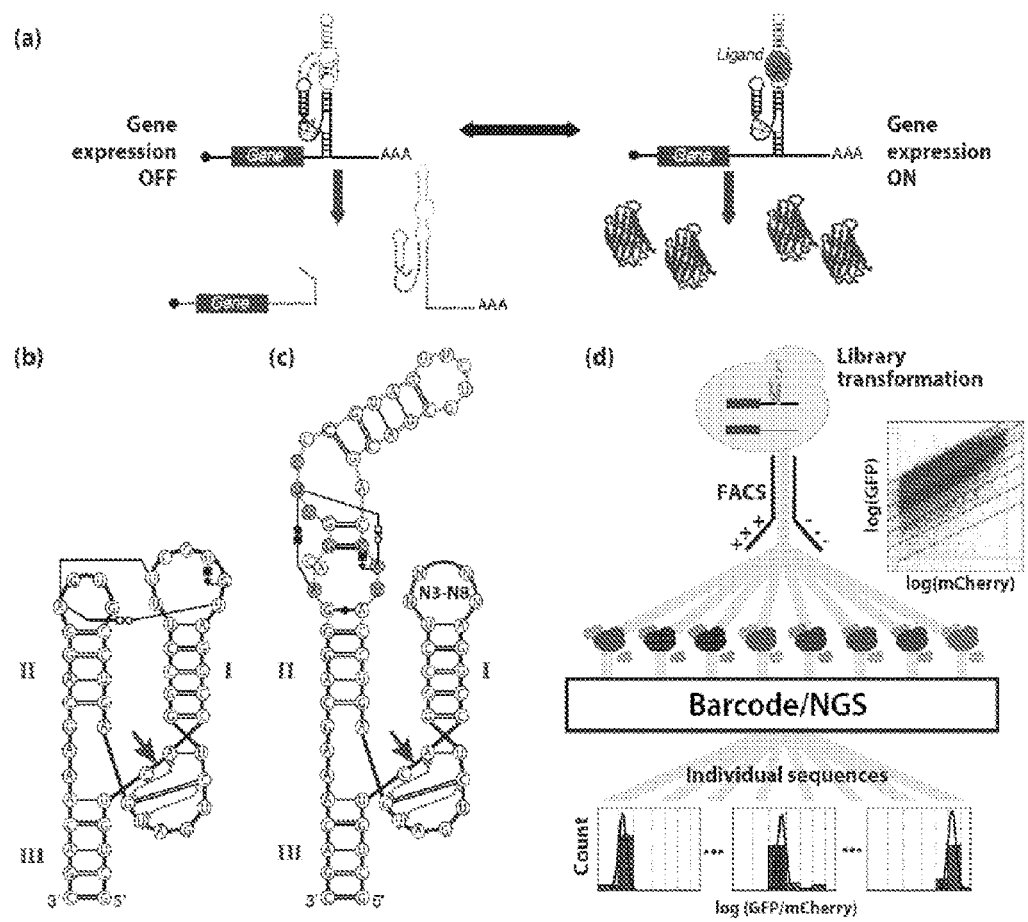
FIG. 1 High-throughput RNA device engineering method. (a) RNA device gene-regulatory mechanism. The RNA device is encoded into the 3' UTR of a gene, such that device cleavage results in transcript destabilization and reduced expression levels. Binding of ligand (blue circle) to the RNA device disrupts tertiary interactions required for self-cleavage, thereby stabilizing the transcript and upregulating gene expression. (b) HHRz (sTRSV) interactions. Interactions are indicated following Leontis-Westhof notation with the addition of green "I-beams" showing non-adjacent base-stacking interactions; the sequence shown is SEQ ID NO: 7 (c) Library design for theophylline-responsive tertiary interaction switches. Loop libraries (N3-N8; green) are grafted onto stem II of the sTRSV HHRz (blue), with the theophylline aptamer (gold) on the opposing stem. The aptamer and loop library sequences replace tertiary-interacting regions of the ribozyme, constituted naturally by loops I and II. Red arrow indicates the ribozyme cleavage site. Nucleotides in contact with the theophylline ligand are indicated in green. The single nucleotide difference between the CAG and AAG aptamer variants is shown with a joint cytosine/adenine nucleotide. The library also contains the corresponding structure with the aptamer grafted onto stem I (not shown); the sequence shown is SEQ ID NO: 22. (d) Overview of the FACS-Seq method for high-throughput RNA device engineering. Device libraries are gap-repaired into a two-color reporter construct in yeast. Cells harboring the libraries are grown under selected conditions and separately sorted 8-ways using gates uniformly log-spaced over the GFP/mCherry ratio (upper-right inset). For each sorted bin, plasmid DNA is extracted and uniquely barcoded before the entire set is mixed and sequenced. The activities ($\mu$) of each sequence for each particular condition are computed from the NGS bin counts.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides, ribonucleotides or a combination thereof, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as an inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

As used herein, the term "oligonucleotide" refers to a multimer of at least 10, e.g., at least 15 or at least 30 nucleotides. In some embodiments, an oligonucleotide may be in the range of 15-200 nucleotides in length, or more.

As used herein, the term "interact in a ligand-dependent manner" refers to an interaction that occurs only in the presence of a ligand, or an interaction that occurs only in the absence of a ligand, but not an interaction that occurs regardless of whether a ligand is present.

As used herein, the term "ligand-responsive" refers to an activity that changes (i.e., increases or decreases) in the presence of a ligand. A change may be decrease of at least 50%, at least 80%, at least 90% or at least 95%, or more, or an increase of at least 2-fold, at least 5-fold, at least 10-fold or at least 50-fold, or more.

Figure 10:
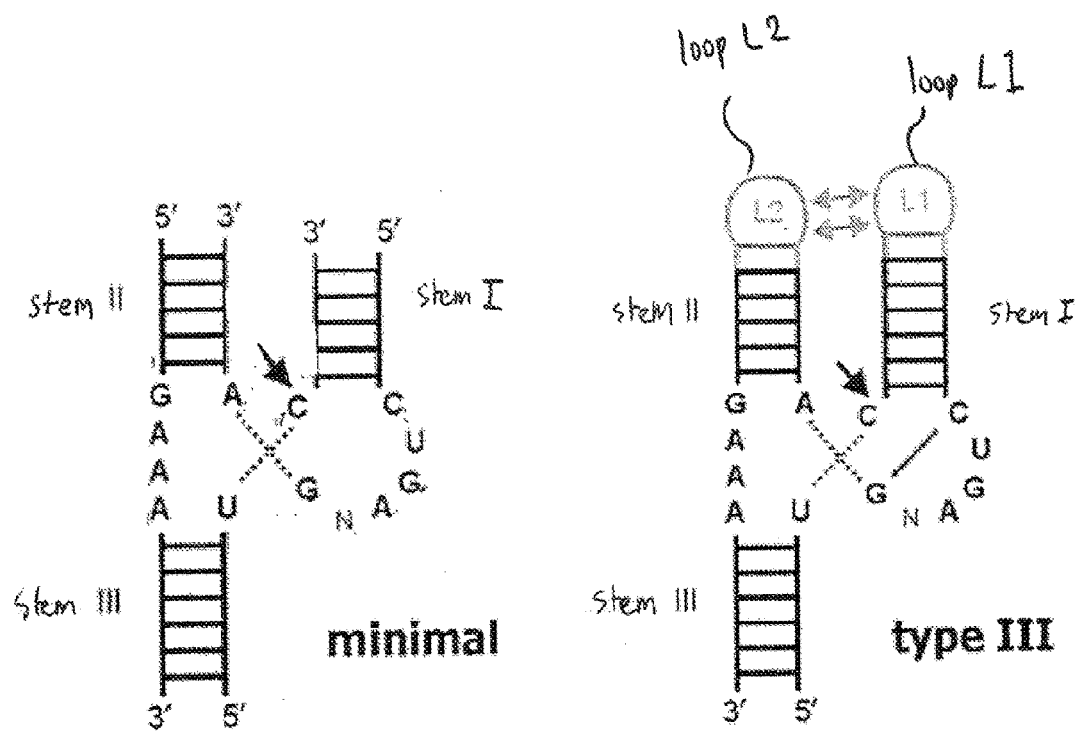
FIG. 10 schematically illustrates the structure of an exemplar minis hammerhead ribozyme and a type III ribozyme.

As used herein, the term "hammerhead ribozyme" refers to a RNA molecule motif that catalyzes reversible cleavage and joining reactions at a specific site within an RNA molecule. The minimal hammerhead ribozyme is composed of three base paired helices, separated by short linkers of conserved sequence as shown in the crystal structure described in Scott (Cell 1995 81: 991-1002). These helices are called I, II and III. The conserved uridine-turn links helix I to helix II and usually contains the sequence CUGA. Helix II and III are linked by a sequence GAAA. The cleavage reaction occurs between helix III and I, and is usually a C. The structure-function relationships in ribozymes have been extensively reviewed (see, e.g., Hammann et al, RNA 2012 18: 871-885). The structure of an exemplary minimal hammerhead ribozyme and a type III ribozyme are shown in FIG. 10. The various parts of a hammerhead ribozyme, e.g., stem I, stem II, stem III, loop L1 and loop L2, etc. are defined with reference to FIG. 10. A ribozyme can contain one or more non-naturally occurring nucleotides, as described above.

As used herein, the term "replaced by" in the context of a loop that is a replaced by an aptamer, refers to a change in which a loop of a ribozyme, but not the stem that terminates in that loop, is swapped out for the sequence of an aptamer. In other words, the nucleotide sequence of the original loop in the parent ribozyme no longer exists at the end of the stem of the ribozyme, or in the aptamer in the product ligand-responsive ribozyme. The stem onto which the aptamer is grafted is not part of the aptamer, in other words, if a loop is a replaced by an aptamer, a stem (stem I or stem II) of the ribozyme is directly connected to the aptamer, without any attempt to preserve the loop that is usually at that position. In some cases, the stem that carries the aptamer, which is left in place during construction of the present ribozyme, may have a wild-type sequence. In some cases, the structure defined by the aptamer and the stem (stem I or stem II) that is connected to the aptamer is at least 20, e.g., at least 25 or at least 30, nucleotides in length. In some cases, the structure is not a simple hairpin composed of a perfectly base paired stem of 4-6 nt and a loop of 5-7 nt, as illustrated in FIG. 1b. Rather, the structure defined by the aptamer and the stem (stem I or stem II) that is connected to the aptamer may contain a perfectly base paired stem of 4-6 nt (which may be derived from the ribozyme being modified and may have a wild type sequence) and a more complicated structure that contains one or more bulges of one or more nucleotides and, and one or more arms, as illustrated in FIG. 1c.

As used herein, the term "RNA aptamer" refers to a single-stranded RNA sequence that can specifically bind to a target molecule (a "ligand") with high affinity. The ligand for an aptamer can be a polypeptide, or a small, non-proteinaceous organic molecule of less than 1 kDa (e.g., less then 500 Da), for example. Aptamers and ways for screening for aptamers that bind to a specific target molecule are well known (see, e.g., Hernandez et al, Curr Top Med Chem. 2015 15:1066-81, Darmostuk et al, Biotechnol Adv. 2015 S0734-9750) and Kang Adv. Biochem. Eng. Biotechnol. 2013 131: 153-69). In some cases, an aptamer may have a molecular weight of 8 kDa-25 kDa. Aptamers can bind a wide variety of exemplary ligands, including, without limitation, small molecules, such as drugs, metabolites, intermediates, cofactors, transition state analogs, ions, metals, nucleic acids, polysaccharides, glycoproteins, hormones, receptors and cell surfaces (such as cell walls and cell membranes), and toxins, aptamers that may be used in the instant invention bind proteins or polypeptides. In particular embodiments, an aptamer may be at least 15, at least 20, at least 25 or at least 30 nucleotides and up to 50, 70 or 100 nucleotides in length. In some embodiments, the aptamer bears no structural or sequence similarity (other than those that occur by chance) with the loop that is replaced by the aptamer, or the stem connected to that loop.

As used herein, the term "modified sequence" refers to a sequence that is not naturally occurring, i.e., not wild-type. For example, if a loop of a ribozyme has a modified sequence, then that loop has a sequence that is not found in the same loop of a wild type ribozyme.

As used herein, the term "autocatalytic cleavage" refers to a reaction in which a ribozyme catalyzes its own cleavage.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The phrase "optical signal" refers to light signal that can be detected by a photodetector, e.g., a light microscope, a spectrophotometer, a fluorescent microscope, a fluorescent sample reader, or a fluorescence activated cell sorter, 3D tomographer, a camera, etc.

The term "optically detectable protein" refers to a protein whose expression can be detected by the presence of an optical signal produced by the protein. An optical signal is produced by a protein, for example, when the protein is capable of being excited by a particular wavelength of light and emits another wavelength of light which is detectable. An optical signal is produced by a protein, for example, when the protein catalyzes a reaction which results in a light signal. Fluorescent proteins, luminescent proteins, etc., are examples of optically detectable proteins.

The term "expression cassette" refers to a nucleic acid sequence comprising a promoter region, a coding sequence, and a 3' untranslated region (UTR).

Other definitions of terms may appear throughout the specification.

DETAILED DESCRIPTION

As noted above, a ligand-responsive hammerhead ribozyme is provided. Relative to a wild-type hammerhead ribozyme (e.g., a type III ribozyme, the structure of which is schematically illustrated in FIG. 10), the ligand-responsive hammerhead ribozyme may comprise a first loop that has been replaced by an RNA aptamer and a second loop that comprises a modified sequence. The first and second loops are loops L1 and L2 respectively, or loops L2 and L1 respectively, meaning that if one of those loops is replaced by the aptamer, the other is modified. For example, in some cases, the first loop is loop L1 and the second loop is loop L2, and in other cases the first loop is loop L2 and the second loop is loop L1.

As will be described in greater detail below, the aptamer and the loop that has the modified sequence interact in a ligand-dependent manner, and autocatalytic cleavage of the ribozyme is ligand-responsive.

As noted above, the aptamer may be directly connected to a stem region of a parent ribozyme, which eliminates the first or second loop from the parent ribozyme. For example, if the loop replaced by the aptamer contains 4 or 5 nucleotides, those nucleotides are not present in the same position in the product ribozyme, or in a loop or bulge in the added aptamer. In some cases, the aptamer may contain a natural stem that can be joined directly to a stem of a parent ribozyme.

In some embodiments, the ribozyme may be a type III hammerhead ribozyme (meaning that there are covalently closed loops at the ends of both stem I and stem II), however the present results are believed to be directly applicable to type I and type II ribozymes (which have a similar structure to type III hammerhead ribozymes (see, e.g., Hammann et al, RNA 2012 18: 871-885)).

In some embodiments, the ribozyme may be active only in the absence of the ligand. In these embodiments, binding of the ligand to the aptamer may cause the first and second loops to disassociate from one another, thereby inhibiting autocatalytic cleavage of the ribozyme.

In other embodiments, the ribozyme may be active only in the absence of the ligand. In these embodiments, binding of the ligand to the aptamer may cause the first and second loops to interact with one another, thereby activating autocatalytic cleavage of the ribozyme.

In some embodiments, ribozyme may comprise at least one modified nucleotide, e.g., at least 2, at least 3, at least 4, at least 5, at least 6, at least 8, at least 9 or at least 10 modified nucleotides.

The aptamer may bind to any type of ligand. An aptamer may be developed to bind particular ligands by employing known in vivo or in vitro (most typically, in vitro) selection techniques known as SELEX (Ellington et al., Nature 346: 818-22, 1990; and Tuerk et al., Science 249, 505-10, 1990). Methods of making aptamers are also described in, for example, US-2009-0082217-A1, U.S. Pat. No. 5,582,981, PCT Publication No. WO 00/20040, U.S. Pat. No. 5,270, 163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291. In some embodiments, the ligand may a non-proteinaceous compound have a molecular weight in the range of 50 to 2,500 Da, e.g., less then 500 Da, less then 400 Da or less then 300 Da, for example. In certain cases, a ligand may be functionally inert relative to the cells housing the ribozyme, thereby allowing the ribozyme to be activated or inactivated in a cellular context without significantly effecting the cell. In other embodiments, the ligand may be produced by the cell that contains the ribozyme, e.g., as a metabolite.

In certain embodiments, the ribozyme being modified may comprise a first stem (i.e., stem I) of 4-7 bp terminating in a loop (loop L1) of 4-100 nt, a second stem (i.e., stem II) of 4-6 bp terminating in a loop (loop L2) of 4-100 nt, and a third stem (stem III) of 3-6 bp, wherein: (i) the first and second stems are joined by sequence CUGANGA, (ii) the second and third stems are joined by sequence GAAA, and (iii) the second and third stems are joined by sequence NUH (IUPAC code), e.g, UC, as illustrated in FIG. 10. In this embodiment, the first stem or the second stem is directly joined by an aptamer (i.e., without the loop that was originally present) and the other of the first or second stems terminates in a loop that contains a modified sequence. As noted above, the aptamer and the modified sequence interact in a ligand-dependent manner and autocatalytic cleavage of the ribozyme is ligand-responsive. In other words, either the first loop or the second loop (i.e., the loops at the end of stems I or II) will be replaced by an aptamer, and the other loop will be modified so that it can interact with the aptamer, resulting in a ligand dependent activity. As will be described in greater detail below, both ends of stem III may be joined to a transcript, so that the transcript can be cleaved in a ligand-dependent manner.

Also provided is a construct comprising a nucleic acid encoding the above-described ribozyme. In certain cases, the nucleic acid is present in an expression cassette comprising: a promoter, a coding sequence, and a 3' UTR, where the ribozyme allows one to regulate expression of the coding sequence in a ligand-specific manner. For example, the nucleic acid may be present in a 3' UTR of the expression cassette, although it can be positioned in other places (e.g., in an intron or in the 5' UTR). The coding sequence may encode a transcription factor, an enzyme, or an optically detectable protein (e.g., GFP or mCherry, a red fluorescent protein from *Discosoma* sp), for example.

Cells containing a construct comprising a nucleic acid encoding the above-described ribozyme is also provided. The cells may be from any species, including eukaryotes and prokaryotes, including plants (e.g., monocots or dicots), bacteria, yeast, and animals (e.g., insects, mammals, fish, reptiles, amphibians), etc. In particular embodiments, the cells may be a mammalian cell, e.g., monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N. Y. Acad. Sci 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209. Methods of introducing constructs into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments, lipofectamine and calcium mediated gene transfer technologies are used. Methods for introducing circular nucleic acids are also well known in the art and discussed in Ausubel, above.

Also provided is a method for modulating expression of a gene. In these embodiments, the method may comprise: contacting a cell (a cell comprising a construct comprising a nucleic acid encoding the above-described ribozyme, where the nucleic acid is present in an expression cassette comprising: a promoter, a coding sequence, and a 3' UTR, and the ribozyme allows one to regulate expression of the coding sequence in a ligand-specific manner) with a ligand for the aptamer, thereby causing the first and second loops to associate or disassociate and modulating expression of the product encoded by the coding sequence. As noted above, in certain cases, binding of the ligand to the aptamer may inhibit autocatytic cleavage of the ribozyme, thereby increasing expression of the product (which may be an RNA or a protein) encoded by the coding sequence. In other embodiments, binding of the ligand to the aptamer induces autocatalytic cleavage of the ribozyme, thereby reducing expression of the product encoded by the coding sequence. As would be apparent, the product may be a protein or a non-coding RNA such as a lncRNA, miRNA/shRNA/siRNA, circRNA, Cas9 guide RNA, or the like.

The ligand may be exogenously added to the cell or may be made by the cell. As would be apparent, the method may further comprise analyzing the cell after expression of the product has been modulated.

The present ligand-responsive hammerhead ribozyme can be used in a variety of applications, such as modulating enzymatic activities, protein-protein interactions, protein-DNA interactions, protein translocation, catalysis, expression of non-coding RNAs and regulation, to ultimately engineer complex networks in mammalian organisms. A coding sequence for the ligand-responsive hammerhead ribozyme can be incorporated into a variety of genes, and the ribozyme can then be used to program proteins involved in a variety of applications, such as gene control, signal transduction, metabolism, subcellular localization, and imaging applications, etc.

In one embodiment, the present ligand-responsive ribozyme can be used in imaging applications. In these embodiments, the aptamer may bind to a cellular metabolite, and binding of the aptamer to the metabolite in the cell modulates expression of a reporter protein (e.g., mCherry or GFP), thereby providing a non-invasive way to image the presence of the metabolite in vivo or in vitro. Alternatively, the present ligand-responsive hammerhead ribozyme can be used to control metabolism or gene expression, e.g., by placing a coding sequence for the ribozyme into an expression cassette encoding an enzyme or transcription factor, for example. In this embodiment, addition of the ligand for the aptamer will change the expression of the enzyme or transcription factor. For example, the present ligand-responsive ribozyme can further be used to engineer novel regulatory pathways and control loops for applications in metabolic engineering (Khosla et al., Nat Rev Drug Discov 2, 1019-25 (2003)) and synthetic circuit design (Kobayashi et al., Proc Natl Acad Sci USA 101, 8414-9 (2004)) by enabling the cell to sense and respond to intracellular metabolite levels and environmental signals. Because the regulated nucleic acids activity is tunable over a range of ligand concentrations, switches can be designed to inhibit or activate genes only when certain metabolites exceed or go below certain concentrations. Balancing heterologous gene expression in biosynthetic pathways (Berens et al., Bioorg Med Chem 9, 2549-56 (2001)) to maximize product yield can be achieved with aptamer-regulated nucleic acids that regulate expression of biosynthetic genes in response to pathway intermediate levels. Synthetic gene circuits have recently been used to understand and model cellular networks (Nagai et al., Nat Biotechnol 20, 87-90 (2002)) and to achieve cellular control as a step towards programmable cell behavior (Watkins et al., Curr Opin Mol Ther 4, 224-8 (2002)). Gene circuits can be built using combinations of aptamer-regulated nucleic acids as regulators for precise control schemes. Aptamer-regulated nucleic acids will be useful tools in building and characterizing circuits that accurately model natural regulatory pathways and yield further insight into these prevalent regulation schemes.

In some embodiments, the present ligand-responsive ribozyme can be used to increase or decrease expression of a guide RNA in a ligand-dependent manner, thereby allowing one to make changes to a genome in a ligand-dependent manner.

A library comprising a plurality of constructs is also provided. In these embodiments, each construct of the library comprises an expression cassette comprising: a) a coding sequence for a reporter protein; and b) a coding sequence for a modified ribozyme, wherein the modified ribozyme comprises i. a first loop that has been replaced by an RNA aptamer that binds to a ligand and ii. a second loop comprising a sequence that varies between the different constructs of the library. This library can be used in a variety of screening methods. In one embodiment, the method may comprise a) introducing the library of claim 1 into a population of cells; b) selecting a sub-population of the cells in which reporter expression is low, thereby identifying cells in which the modified ribozymes are catalytically active in the absence of the ligand; c) separately binning cells selected in b) that i. have and ii. have not been exposed to the ligand, based on the expression of the reporter protein; d) sequencing the modified ribozymes of the binned cells of c); and e) identifying sequence that is in a bin of i. and a bin of ii., thereby identifying a ribozyme that has an autocatalytic activity that is inducible by the ligand. Similar methods may be employed to identify ribozymes that have an autocatalytic activity that is inhibited by the ligand.

EXAMPLES

In order to further illustrate the present invention, the following specific examples are given with the understanding that they are being offered to illustrate the present invention and should not be construed in any way as limiting its scope.

Described here is a framework for engineering RNA devices from preexisting aptamers that exhibit ligand-responsive ribozyme tertiary interactions. The methodology utilizes cell sorting, high-throughput sequencing, and statistical data analyses to enable parallel measurements of the activities of hundreds of thousands of sequences from RNA device libraries in the absence and presence of ligands. The tertiary interaction RNA devices exhibit improved performance in terms of gene silencing, activation ratio, and ligand sensitivity as compared to optimized RNA devices that rely on secondary structure changes. This method is applied to build biosensors for diverse ligands and determine consensus sequences that enable ligand-responsive tertiary interactions. These methods allows one to develop broadly applicable genetic tools and to elucidate understanding of the underlying sequence-structure-function relationships that empower rational design of complex biomolecules.

Example 1

Simultaneously Assaying all Members of an RNA Device Library

A platform modulating HHRz tertiary interactions (FIG. 1a) may achieve improved performance by eliminating the slow secondary structure conformational change, thereby supporting ribozymes with faster cleavage kinetics. Since ribozyme tertiary interactions are only functionally conserved, a library framework that supports the creation of RNA devices with ligand-responsive tertiary interactions were screened for functional sequences. Our hypothesis that it is possible to build RNA devices that function based on interference with the tertiary interactions between the two loops of a HHRz (FIG. 1b) relies on (i) the ability to obtain catalytic activity in a ribozyme with an arbitrary sequence on one loop by varying the opposite loop sequence, and (ii) target molecule binding to an aptamer on one loop interfering with that activity. The first property allows replacing one of the ribozyme loops with an aptamer for an arbitrary target and identifying a corresponding sequence on the opposite loop that restores cleavage activity in the absence of target (FIG. 1c). The second property allows this structure to behave as a switch through ligand binding to the aptamer interfering with the tertiary interactions.

Tertiary interaction switch libraries were designed based on the theophylline aptamer and assayed the activities of all library members using a massively parallel FACS-Seq method (FIG. 1d). The libraries were designed based on modifying the loop sequences of the tobacco ringspot virus (sTRSV) HHRz. One of two theophylline aptamer variants was grafted onto the ribozyme to replace either loop I or II, while the opposite loop was substituted with a library of all possible sequences ranging in length from three to eight nucleotides (FIG. 1c), requiring a library size of 349,440 sequences not including controls. The in vivo gene-regulatory activity of every library member was simultaneously measured through a FACS-Seq assay (FIG. 1d). The RNA device libraries were cloned by gap-repair into the 3' untranslated region (UTR) of a reporter construct (encoding GFP), where cleavage of the reporter transcript (or high ribozyme activity) results in low GFP expression (see Liang, et al. *Nucleic Acids Res.* 40, e154 (2012)). The reporter construct was placed within a low-copy plasmid that harbored a second reporter construct (encoding mCherry) that served as a control to normalize for cell-to-cell variability in gene expression.

Following transformation and cell growth, populations harboring the RNA device library were FACS-sorted to enrich for cells exhibiting a reduced GFP/mCherry expression ratio ($\mu$), indicative of ribozyme catalytic activity. This initial sort served to enrich the population of cells for those harboring sequences with self-cleavage activity, which are more likely to exhibit expression levels modulated by the presence of the target. The prescreened cells were grown separately in the presence and absence of ligand, and individual cells from these populations were sorted based on the measured GFP/mCherry ratio ($\mu$) into eight different bins. Library members in each bin were recovered through plasmid extraction and separately barcoded. An NGS analysis determined the frequency of occurrence of each library member in the different activity bins as a function of ligand condition (FIG. 1d). Biological replicates were carried forward at every step of the process, starting from parallel library-scale transformations.

Figure 2:
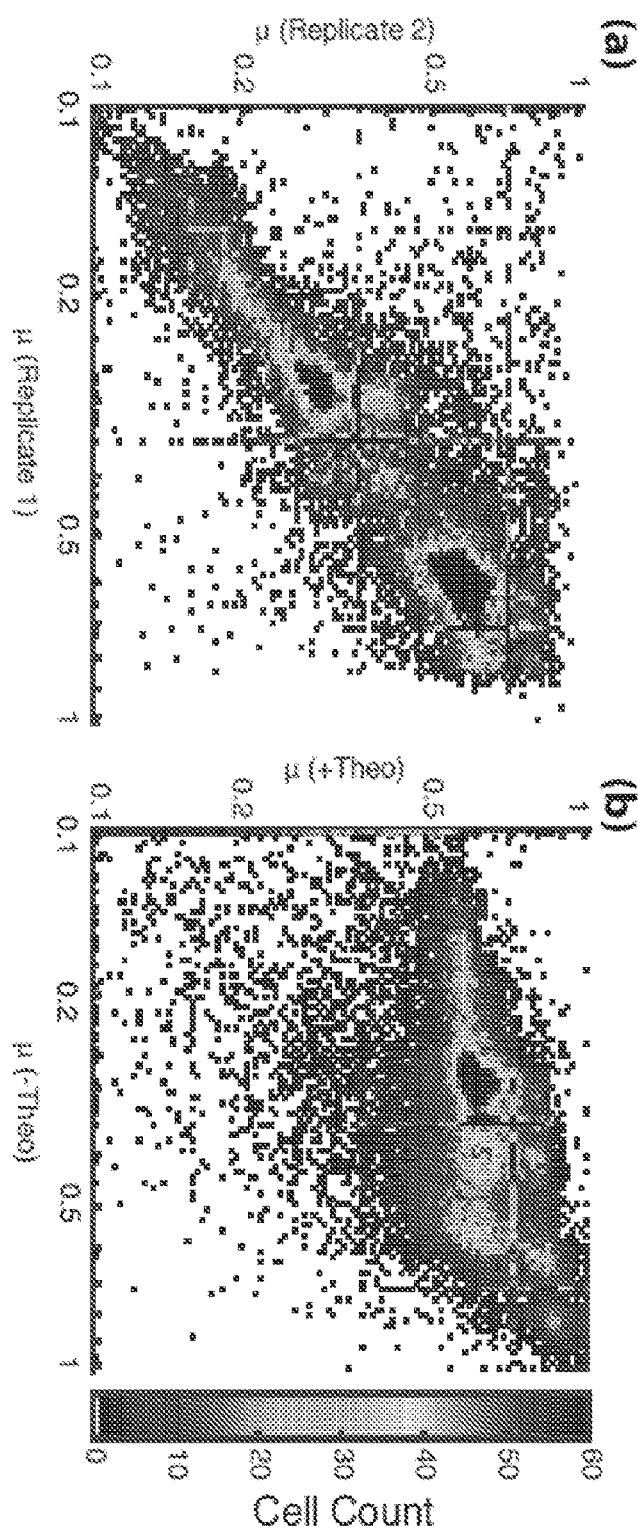
FIG. 2 GFP/mCherry activity ratios ($\mu$) for all members of the theophylline aptamer libraries based on FACS-Seq assays. Each point on the plots represents a unique library sequence that has the indicated GFP/mCherry values under the specified conditions. (a) GFP/mCherry values ($\mu$) for theophylline aptamer library members from the two replicate runs without target present (N=5,389). (b) GFP/mCherry values ($\mu$) for theophylline aptamer library members in the presence (5 mM) and absence of theophylline (N=16,024; combined replicate data). Only data for which at least 50 cells were counted is used in each analysis. The striations at particular values result from sequences for which all NGS reads for that sequence were from the same FACS bin, resulting in an estimate at the midpoint of the bin.

Data were analyzed to reduce the bin counts into a point estimate for $\mu$ for each library sequence. Under the no-theophylline condition, most sequences in the prescreened library showed low $\mu$ with a median value of 0.30 for both replicates (FIG. 2a). These results indicated that the pre-screen selection was effective at enriching for cells that exhibit low GFP/mCherry ratio in the absence of ligand. In the presence of theophylline, both replicates exhibited higher $\mu$ with median values of 0.62 and 0.61 for the replicates (FIG. 2b). The majority of the sequences exhibited switching (73% have a fold change of at least 1.3), with the activation ratio of the switch predominantly determined by the basal GFP level in the absence of theophylline. Trends observed in the data are consistent with our hypothesis of competition between binding of the target to the aptamer loop and tertiary interactions resulting in self-cleavage.

Example 2

Identifying Highly Functional Tertiary Interaction Switches

The FACS-Seq method can rapidly assess in vivo activities of large libraries of RNA devices. These data can be mined to identify sequences that result in highly functional gene-regulatory switches. Seventeen sequences from our theophylline aptamer library, five with the CAG aptamer variant and twelve with the AAG variant, that exhibit the largest activation ratios (Table 1) to validate through additional characterization assays.

TABLE 1

Flow cytometry validation results for switch sequences identified from NGS analyses.

| Loop I | Loop II | $\mu$ (-tgt) | $\mu$ (+tgt) | Activation Ratio |
|---|---|---|---|---|
| Theo (AAG) | AAAAA | 0.056 ± 0.002 | 0.51 ± 0.07 | 9.1 ± 1.3 |
| Theo (AAG) | CAGAA | 0.158 ± 0.006 | 1.26 ± 0.09 | 7.9 ± 0.4 |
| Theo (CAG) | CAGUA | 0.165 ± 0.014 | 1.14 ± 0.08 | 6.9 ± 0.2 |
| Theo (CAG) | AGGAAA | 0.236 ± 0.020 | 1.60 ± 0.22 | 7.0 ± 1.5 |
| Theo (CAG) | CAGAGAA | 0.159 ± 0.010 | 0.87 ± 0.11 | 5.5 ± 0.7 |
| GGAACU | Theo (AAG) | 0.164 ± 0.008 | 0.93 ± 0.04 | 5.7 ± 0.4 |

TABLE 1-continued

Flow cytometry validation results for switch sequences identified from NGS analyses.

| Loop I | Loop II | μ (-tgt) | μ (+tgt) | Activation Ratio |
|---|---|---|---|---|
| Theo (AAG) | AGAGA | 0.107 ± 0.003 | 1.03 ± 0.07 | 9.6 ± 0.5 |
| Theo (AAG) | AAAGA | 0.088 ± 0.003 | 1.00 ± 0.08 | 11.4 ± 0.8 |
| Theo (AAG) | CAAUAA | 0.144 ± 0.008 | 0.98 ± 0.04 | 6.9 ± 0.5 |
| Theo (CAG) | CAGAUAAA | 0.238 ± 0.012 | 1.23 ± 0.08 | 5.2 ± 0.2 |
| Theo (CAG) | CACGUGAA | 0.232 ± 0.003 | 1.40 ± 0.20 | 6.0 ± 0.8 |
| Theo (AAG) | CAUAUAA | 0.205 ± 0.006 | 1.58 ± 0.15 | 7.8 ± 0.9 |
| Theo (AAG) | CAAGUGAA | 0.230 ± 0.007 | 1.90 ± 0.37 | 8.2 ± 1.4 |
| Theo (AAG) | CAAUUAA | 0.183 ± 0.011 | 1.40 ± 0.15 | 7.6 ± 0.6 |
| Theo (AAG) | CAAUCUAA | 0.200 ± 0.011 | 1.56 ± 0.12 | 7.8 ± 0.3 |
| Theo (AAG) | CAUGUAAA | 0.207 ± 0.010 | 1.80 ± 0.12 | 8.8 ± 1.0 |
| ACUUUAA | Theo (AAG) | 0.174 ± 0.006 | 1.27 ± 0.01 | 7.3 ± 0.2 |
| Tetracycline | AGGUAUGA | 0.196 ± 0.006 | 1.80 ± 0.07 | 9.1 ± 0.2 |
| GGGGGUGC | Tetracycline | 0.154 ± 0.005 | 1.16 ± 0.04 | 7.5 ± 0.2 |
| GGGAUUAU | Tetracycline | 0.129 ± 0.007 | 0.92 ± 0.18 | 7.0 ± 1.0 |
| GGGUAGAU | Tetracycline | 0.240 ± 0.012 | 1.28 ± 0.07 | 5.3 ± 0.1 |
| AGGGAAAU | Tetracycline | 0.173 ± 0.010 | 1.17 ± 0.10 | 6.8 ± 0.3 |
| Neomycin | UGUAGCGG | 0.376 ± 0.012 | 2.43 ± 0.11 | 6.5 ± 0.3 |
| Neomycin | CUGGCCAC | 0.406 ± 0.009 | 2.34 ± 0.07 | 5.8 ± 0.1 |
| Neomycin | CCGGCCAC | 0.316 ± 0.008 | 1.95 ± 0.10 | 6.2 ± 0.3 |
| AGGACUAA | Neomycin | 0.595 ± 0.024 | 2.13 ± 0.15 | 3.6 ± 0.1 |

The values of μ were determined from flow cytometry analysis of at least 3 independent transformants containing the indicated switch. Error estimates are the standard error of the mean.

Figure 3:
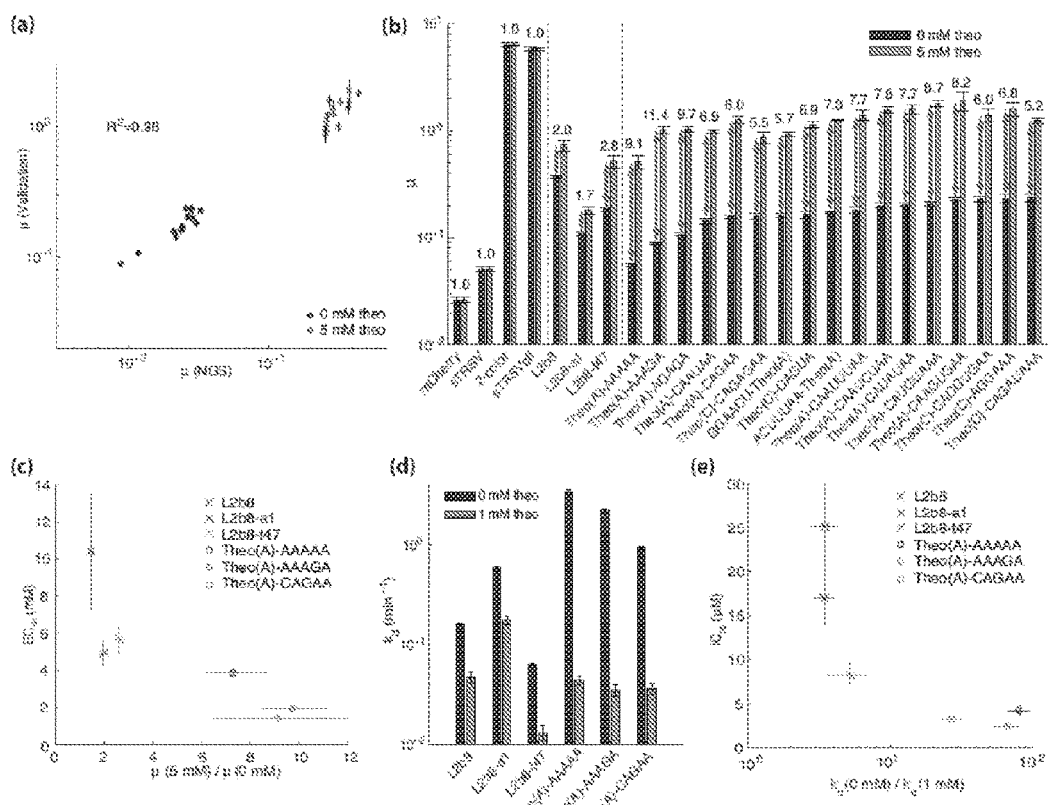
FIG. 3 Validation of theophylline-responsive tertiary interaction switches identified through the FACS-Seq method. (a) Comparison of NGS- and flow cytometry-based GFP/mCherry activity measurements ($\mu$) for individual library members. Each point (N=30) is a single library sequence identified from the NGS analysis. Values are reported at 0 mM (red) and 5 mM (blue) theophylline. Error bars for the flow cytometry validation represent the standard error of the mean over at least three biological replicates from independent transformants. Error bars for measurements from the NGS analysis represent the range covered by two biological replicates. (b) Flow cytometry-based activity measurements for selected theophylline-responsive switches identified from the NGS analysis. Median GFP/mCherry ratios are reported for cells harboring the indicated switches and controls grown in 0 mM (red) and 5 mM (blue) theophylline. Activation ratios are reported above each construct. Error bars represent standard error of each mean over at least three biological replicates from independent transformants. (c) $EC_{50}$ values versus activity ratios for theophylline-responsive switches (cross, secondary structure device; circle, tertiary interaction device). Flow cytometry data were fit to a 4-parameter logistic model with the Hill slope fixed at 1.0, from which the $EC_{50}$ and 80% confidence interval were determined. Activity ratio is reported as the ratio of $\mu$ for switches grown in 0 and 5 mM theophylline; error bars indicate standard deviation over four biological replicate experiments for each condition. (d) Ribozyme dissociation rate constants as measured through a SPR cleavage assay for devices measured at 0 mM (red) and 1 mM (blue) theophylline. Error bars represent the standard error of the mean from at least triplicate assays. (e) $IC_{50}$ values versus dissociation rate ratios for theophylline-responsive switches (cross, secondary structure device; circle, tertiary interaction device). For each condition, the measurements from at least three separate sets of assays were fit to a 4-parameter logistic model with the Hill slope fixed at 1.0, to compute an $IC_{50}$ value for each set. Dissociation rate ratio is reported as the ratio of $k_d$ at 0 and 1 mM theophylline; error bars represent the 80% confidence interval for the fitted values.
Figure 4:
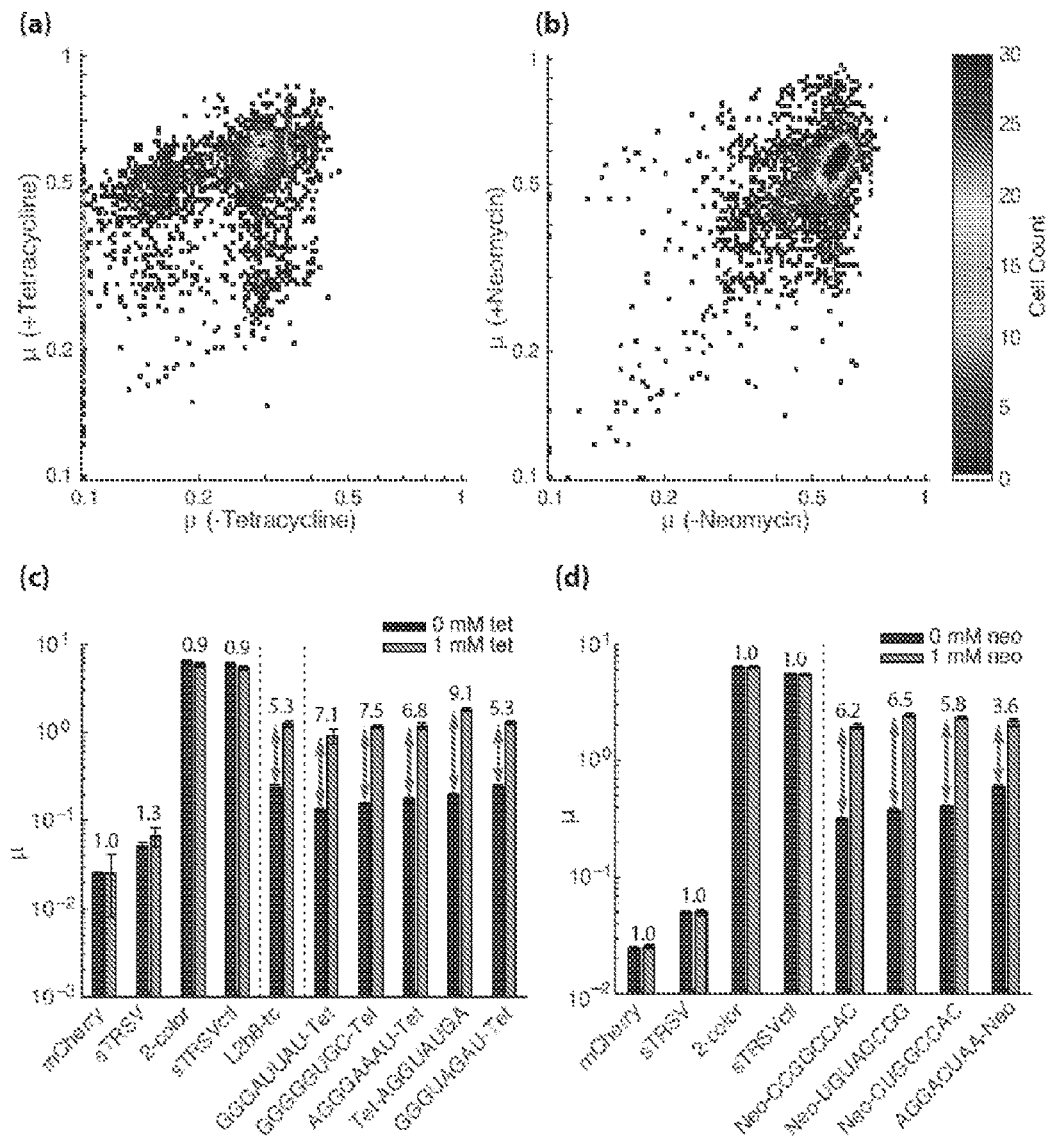
FIG. 4 Extension of the FACS-Seq method to identifying tertiary interaction switches for other aptamer-target pairs. (a, b) GFP/mCherry ratios ($\mu$) for tetracycline (a) and neomycin (b) aptamer library members in the presence and absence of target based on FACS-Seq assays. Each point on the plots represents a unique library sequence (tetracycline: N=3,873; neomycin: N=5,286; combined replicate data) that has the indicated (by color) $\mu$ under the specified conditions. Only sequences for which at least 50 cells were counted over the two combined replicates are used in each analysis. (c, d) Flow cytometry-based activity measurements for selected tetracycline-responsive (c) and neomycin-responsive (d) switches identified from the NGS analysis. Median GFP/mCherry ratios are reported for cells harboring the indicated switches and controls grown in the absence (red) and presence (blue; tetracycline: 1 mM, neomycin: 0.1 mM) of target. Error bars represent the standard error of the mean over at least three biological replicates. Activation ratios are reported above each construct. Vertical dotted lines separate ribozyme/controls, secondary structure switches, and tertiary structure switches. Additional compensation was performed for samples containing tetracycline due to fluorescence properties of this molecule.
Figure 5:
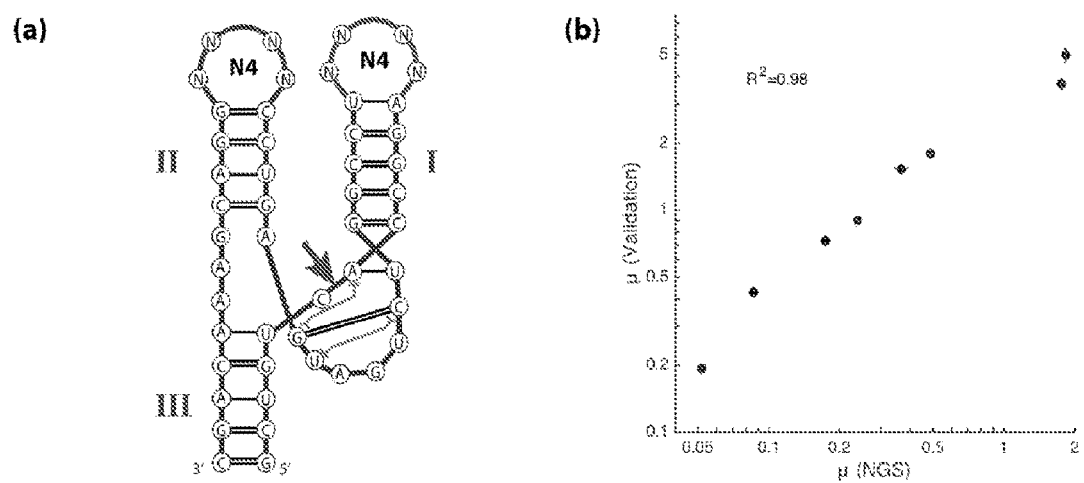
FIG. 5 Validation of an N4/N4 ribozyme library. (a) Library design for N4/N4 ribozyme tertiary interactions. Shown are loop libraries (N4/N4; green/brown) grafted onto stems I and II of the sTRSV hammerhead ribozyme (blue). Red arrow indicates the ribozyme cleavage site in the backbone; the sequence shown is SEQ ID NO: 23. (b) Comparison of NGS- and flow cytometry-based GFP/mCherry activity measurements for individual N4/N4 library members. Each point is a single library sequence that was identified from the NGS analysis. Error bars for the flow cytometry validated measurements represent the standard error of the mean over at least three biological replicates. Error bars for measurements from the NGS analysis represent the range over the two biological replicates.
Figure 6:
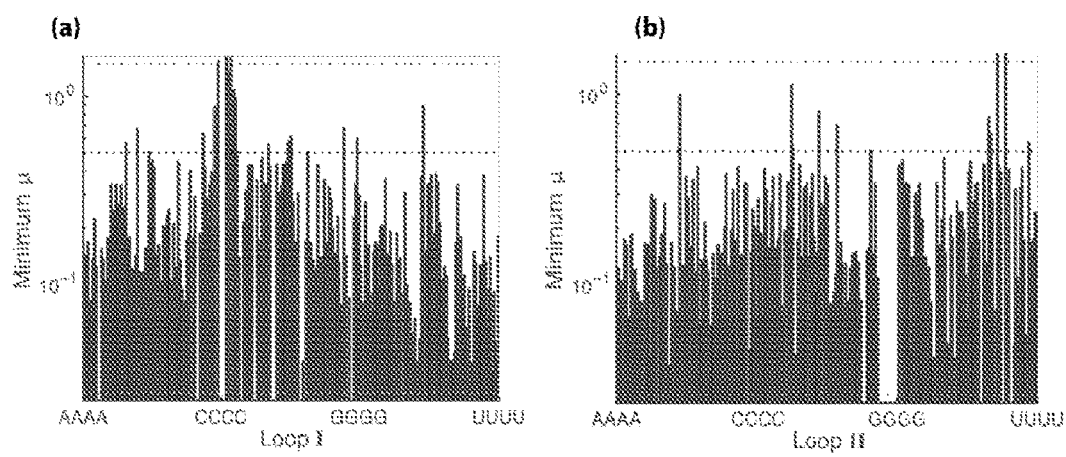
FIG. 6 GFP/mCherry activities ($\mu$) of N4/N4 ribozyme library members for fixed values of one loop. Minimum $\mu$ values observed over all sequences as a function of the sequence on loop I (a) and loop II (b) are shown. In each case, a total of 2,174 sequences (for which at least 100 cells were measured) were considered. Activities for sTRSV (green; lower), sTRSVctl (red; upper), and N4/N4 library mean (black; central) are shown as dotted lines. Note that coverage at the level of cell counts was low, with ~5-10 distinct opposite loop sequences available from which to select the minimum for each loop. Thus, the minimum reported values are an upper bound on the minimum attainable if all 256 opposite loops were considered.
Figure 7:
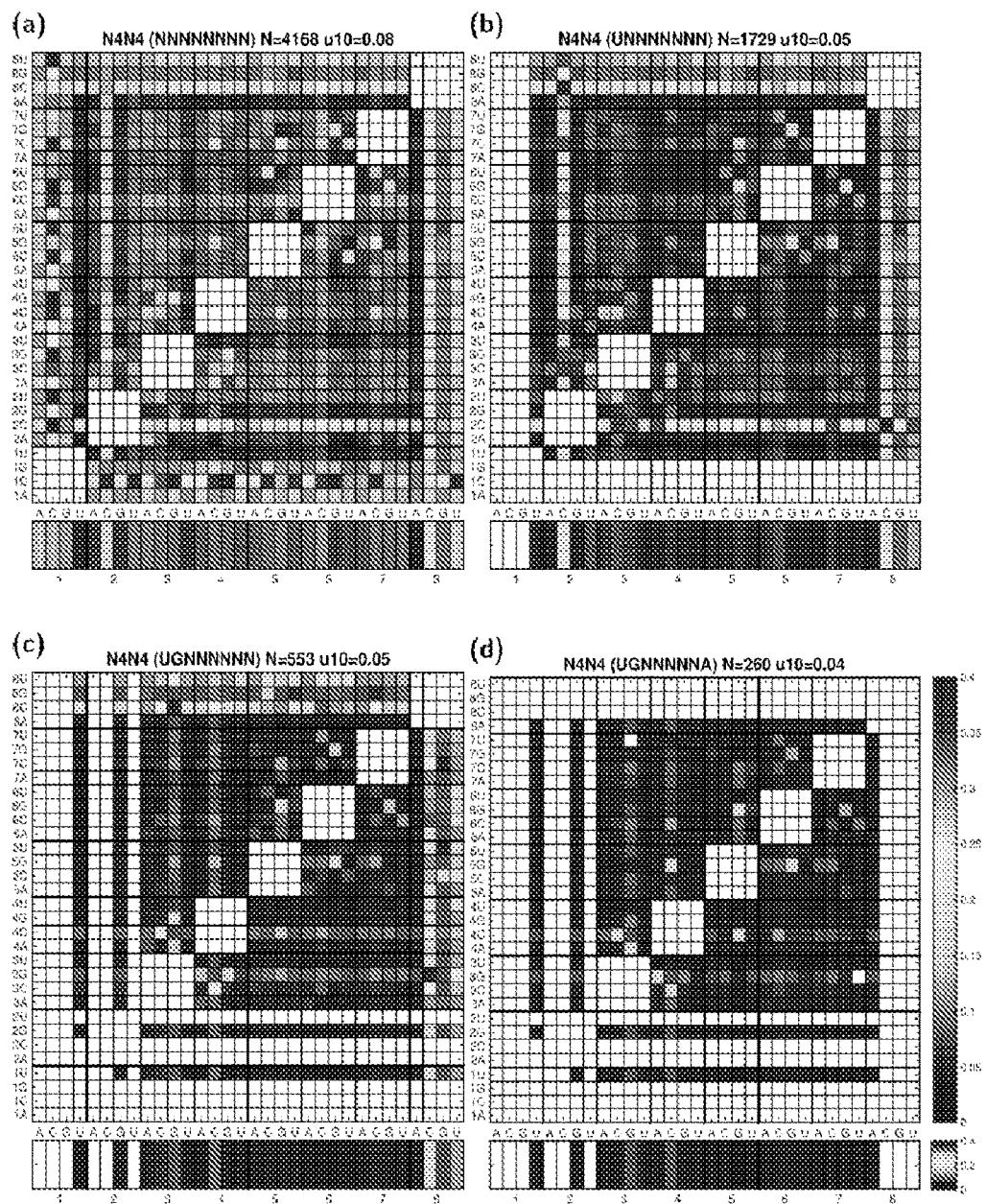
FIG. 7 Effect of loop sequence on activity of the N4/N4 ribozymes. Each panel shows $10^{th}$-percentile $\mu$ values, as a pairwise function of the identity of the four randomized nucleotides on each stem of a ribozyme, averaged over all other nucleotide possibilities in the remaining position. The narrow strip along the bottom of each plot shows the effect of each nucleotide by itself. Lower values of $\mu$ indicate higher levels of ribozyme catalytic activity. Sequence positions are labeled 5' to 3' starting with the four nucleotides on loop I followed by the four nucleotides on loop II. (a) Sequence analysis based on iterating over all possible values of two nucleotides and averaging over all possibilities for the remaining six nucleotides in the loops. The strongest single nucleotide positive effect on catalytic activity arises when position 1 as a U. There is also a strong negative effect of a C in position 1. (b) Sequence analysis based on fixing position 1 as a U and averaging over the remaining five nucleotides for each entry. The dominant positive effect on catalytic activity is observed when position 2 is a G. (c) Sequence analysis based on fixing position 1 as a U and position 2 as a G and averaging over the remaining four nucleotides for each entry. The strongest effect on catalytic activity is observed when position 8 is an A. (d) Sequence analysis based on fixing position 1 as a U, position 2 as a G, and position 8 as an A and averaging over the remaining three nucleotides for each entry. With the consensus sequences set to UGNNNNNNA, the $10^{th}$-percentile $\mu$ is 0.04.
Figure 8:
FIG. 8 GFP/mCherry activities ($\mu$) of N4/N4 ribozyme library members. Activities are shown only for those sequences that had at least 100 cells sorted. Activities for sTRSV (green; lower) and sTRSVctl (red; upper) are shown as dotted lines.

The RNA devices were individually synthesized, integrated into the two-color characterization plasmid, and assayed in yeast via flow cytometry. The μ values obtained from flow cytometry analysis of the reconstructed sequences are tightly correlated with those obtained through the FACS-Seq analysis (FIG. 3a; $R^2$=0.98). We compared the validated activation ratios ($\mu_{-target}/\mu_{+target}$) for several of the best performing switches from the tertiary interaction switch libraries with those from previously optimized RNA devices that function through secondary structure rearrangements (FIG. 3b, Table 1). The data indicated that the switches identified from the tertiary interaction switch libraries exhibit higher activation ratios (11.4±0.8 fold change for Theo(A)-AAAGA, 2.8±0.3 for L2b8-t47, where L2b8 and its variants refer to secondary-structure switching devices) and stringencies (basal level of 0.056±0.002 for Theo(A)-AAAAA, 0.109±0.004 for L2b8-a1) than those that function through secondary-structure switching mechanisms. These values compare favorably with the basal level attainable by the wild-type ribozyme (sTRSV; μ=0.051±0.003), whereas the inactive control ribozyme (sTRSVctl; Table 2) exhibits a μ of 5.8±0.3.

TABLE 2

Sequences of spacers, ribozymes, aptamers, switches, and primers.

| Type | Name | Sequence |
|---|---|---|
| RNA device | L2b8[14] | AAACAAACAAAGCUGUCACCGGAUGUGCUUUCCGGUCUGAUGA<br>GUCCGUUGUCCAUACCAGCAUCGUCUUGAUGCCCUUGGCAGG<br>GACGGGACGGAGGACGAAACAGCAAAAAGAAAAAUAAAAA<br>(SEQ ID NO: 1) |
| RNA device | L2b8-a1[14] | AAACAAACAAAGCUGUCACCGGAAUCAAGGUCCGGUCUGAUGA<br>GUCCGUUGUCCAUACCAGCAUCGUCUUGAUGCCCUUGGCAGG<br>GACGGGACGGAGGACGAAACAGCAAAAAGAAAAAUAAAAA<br>(SEQ ID NO: 2) |

TABLE 2-continued

Sequences of spacers, ribozymes, aptamers, switches, and primers.

| Type | Name | Sequence |
|---|---|---|
| RNA device | L2b8-t47[14] | AAACAAACAAAGCUGUCACCGGAUGUGCUUUCCGGUCUGAUGA GUCCGUUGAGUAUACCAGCAUCGUCUUGAUGCCCUUGGCAGA CUGUAUACGGAGGACGAAACAGCAAAAAGAAAAAUAAAAA (SEQ ID NO: 3) |
| Spacer | 5'(W) | AAACAAACAAA (SEQ ID NO: 4) |
| Spacer | 3'(X) | AAAAAGAAAAAUAAAAA (SEQ ID NO: 5) |
| Spacer | 5' SPR (SPR-fwd) | GGGAAACAAACAAAGUUGUUUU (SEQ ID NO: 6) |
| Spacer | 3' SPR (SPR-rev) | UUUGUU |
| Ribozyme | sTRSV | GCUGU C ACCGGA UGUGCUU UCCGGUCUGAUGA GUCC GUGA GGAC GAA ACAGC (SEQ ID NO: 7) |
| Ribozyme | sTRSVctl | GCUGU C ACCGGA UGUGCUU UCCGGUACGUGAG GUCC GUGA GGAC AGA ACAGC (SEQ ID NO: 8) |
| Aptamer | Theophylline (CAG-variant) | AUACCAGCAUCGUCUUGAUGCCCUUGGCAG (SEQ ID NO: 9) |
| Aptamer | Theophylline (AAG-variant) | AUACCAGCAUCGUCUUGAUGCCCUUGGAAG (SEQ ID NO: 10) |
| Aptamer | Neomycin | GCUUGUCCUUUAAUGGUCC (SEQ ID NO: 11) |
| Aptamer | Tetracycline | AAAACAUACCAGAUUUCGAUCUGGAGAGGUGA AGAAUUCGACCACCU (SEQ ID NO: 12) |
| Library | Loop I Integration | AAACAAACAAA GCUGU C ACCGGA <Aptamer> UCCGGUCUGAUGA GUCC <N3:N8> GGAC GAA ACAGC AAAAAGAAAAAUAAAAA (SEQ ID NO: 13) |
| Library | Loop II Integration | AAACAAACAAA GCUGU C ACCGGA <N3:N8> UCCGGUCUGAUGA GUCC <Aptamer> GGAC GAA ACAGC AAAAAGAAAAAUAAAAA (SEQ ID NO: 13) |
| Primer | T7_W_Primer | AATTTAATACGACTCACTATAGGG AAACAAACAAA GCTGTC ACCGGA (SEQ ID NO: 14) |
| Primer | X_Primer | TTTTTATTTTTCTTTTT GCTGT TTC GTCC (SEQ ID NO: 15) |
| Primer | SPR_fwd_primer | TTCTAATACGACTCACTATAGGG (SEQ ID NO: 16) |
| Primer | SPR_rev_primer | AACAAAGCTGTTTCGTCC (SEQ ID NO: 17) |
| SPR template | L2b8_SPR | TTCTAATACGACTCACTATAGGGGGAAACAAACAAAGTTGTTTTGC TGTCACCGGATGTGCTTTCCGGTCTGATGAGTCCGTTGTCCATACCA GCATCGTCTTGATGCCCTTGGCAGGGACGGGACGGAGGACGAAAC AGCTTTGTT (SEQ ID NO: 18) |
| SPR template | L2b8-a1_SPR | TTCTAATACGACTCACTATAGGGGGAAACAAACAAAGTTGTTTT GCTGTCACCGGAATCAAGGTCCGGTCTGATGAGTCCGTTGTCCAT ACCAGCATCGTCTTGATGCCCTTGGCAGGGACGGGACGGAGGAC GAAACAGCTTTGTT (SEQ ID NO: 19) |
| SPR template | L2b8-t47_SPR | TTCTAATACGACTCACTATAGGGGGAAACAAACAAAGTTGTTTT GCTGTCACCGGATGTGCTTTCCGGTCTGATGAGTCCGTTGAGTATA CCAGCATCGTCTTGATGCCCTTGGCAGACTGTATACGGAGGACGA AACAGCTTTGTT (SEQ ID NO: 20) |
| SPR template | Theo (A)-AAAGA_SPR | TTCTAATACGACTCACTATAGGGAAACAAACAAAGTTGTTTTGCTG TCACCGGAATACCAGCATCGTCTTGATGCCCTTGGAAGTCCGGTCT GATGAGTCCAAAAAGGACGAAACAGCTTTGTT (SEQ ID NO: 21) |
| SPR template | Theo (A)-AAAAA_SPR | TTCTAATACGACTCACTATAGGGAAACAAACAAAGTTGTTTTGCTG TCACCGGAATACCAGCATCGTCTTGATGCCCTTGGAAGTCCGGTCT GATGAGTCCAAAAAGGACGAAACAGCTTTGTT (SEQ ID NO: 21) |
| SPR template | Theo (A)-CAGAA_SPR | TTCTAATACGACTCACTATAGGGAAACAAACAAAGTTGTTTTGCTG TCACCGGAATACCAGCATCGTCTTGATGCCCTTGGAAGTCCGGTCT GATGAGTCCAAAAAGGACGAAACAGCTTTGTT (SEQ ID NO: 21) |

Primers are DNA oligonucleotide sequences and SPR templates are dsDNA for transcribing into RNA for the SPR-based experiments. All other sequences are RNA.

For a subset of the theophylline-responsive switches, we measured the activity as a function of target concentration by performing dose-response assays on reconstructed sequences (FIG. 3c, Table 3). The data shows that compared to the secondary-structure switching devices, the identified tertiary interaction switch devices exhibit greater maximal activation ratios (fold change at 5 mM theophylline: ≥7.3 for tertiary interaction devices, ≤2.6 for secondary-structure switching device) and ligand sensitivities (mean $EC_{50}$ of 7.0 µM for secondary-structure switching devices and 2.4 µM for tertiary interaction devices).

the tertiary interaction devices with the average over the secondary-structure switching devices (FIG. 3e; $IC_{50}$: 3.3 µM for tertiary interaction devices, 17 µM for secondary-structure switching devices). These data support the in vivo findings and indicate that improved cleavage activity and ligand sensitivity can be achieved with the tertiary interaction architecture.

Example 3

Design-Level Modularity is Extendable to Other Aptamers

The widespread applicability of the tertiary interaction switching architecture relies on the ability to restore activity

TABLE 3

Dose-response parameters from flow cytometry for theophylline-responsive RNA devices.

| RNA Device | $EC_{50}$ (mM) | µ (0 mM theophylline) | µ (5 mM theophylline) | Activation Ratio |
|---|---|---|---|---|
| L2b8 | 4.9 [4.3-5.6] | 0.67 [0.63-0.72] | 1.32 [1.22-1.43] | 2.0 [1.8-2.2] |
| L2b8-a1 | 10.4 [7.3-13.5] | 0.19 [0.18-0.21] | 0.28 [0.25-0.32] | 1.5 [1.3-1.7] |
| L2b8-t47 | 5.7 [4.9-6.4] | 0.35 [0.32-0.39] | 0.92 [0.85-1.01] | 2.6 [2.3-3.0] |
| Theo(A)-AAAAA | 3.8 [3.6-4.1] | 0.09 [0.08-0.10] | 0.68 [0.60-0.77] | 7.3 [6.2-8.6] |
| Theo(A)-AAAGA | 1.9 [1.8-2.1] | 0.16 [0.14-0.18] | 1.53 [1.30-1.81] | 9.8 [7.9-12.1] |
| Theo(A)-CAGAA | 1.5 [1.3-1.6] | 0.25 [0.24-0.26] | 2.29 [1.66-3.16] | 9.1 [6.6-12.6] |

Median GFP/mCherry ratios were computed for at least triplicate independent cultures assayed at theophylline concentrations of 0, 0.16, 0.31, 0.62, 1.25, 2.5, 5, 10, and 20 mM. The data were fit to a 4-parameter logistic model with the Hill slope fixed at 1.0; the 80% confidence interval for the $EC_{50}$ fit is shown. A range of one standard deviation over the replicates is shown for the mean activity levels and activity ratio.

Activities and ligand sensitivities were further investigated using an in vitro SPR-based cleavage assay. It was observed that the highest in vitro cleavage activities of the tertiary interaction devices are ~6-fold higher than that of the highest previously-designed secondary-structure switching devices in the absence of ligand (FIG. 3d; $k_d$: 3.5 $min^{-1}$ for Theo(A)-AAAAA, 0.6 $min^{-1}$ for L2b8-a1) and ~4-fold lower in the presence of 1 mM theophylline (FIG. 3d; $k_d$: 0.044 $min^{-1}$ for Theo(A)-AAAAA, 0.17 $min^{-1}$ for L2b8-a1). The ligand concentration at which the cleavage kinetics are half-maximal is 5-fold lower, comparing the average over to a ribozyme that has one loop sequence modified by integration of an aptamer. Restoration of cleavage activity is accomplished through the selection of an appropriate opposite loop sequence that restores tertiary interactions and geometries conducive to self-cleavage. The generality of this strategy was investigated, by characterizing the activities of all members of a HHRz library with loops I and II randomized. It was verified HHRz library members activities span a wide range of activities, with consistent coverage from the activity level of the wildtype (sTRSV) HHRz to the inactive control (FIGS. 4-8). This graded ribozyme library also provides a new genetic tool for modulating gene expression levels over a 77-fold range through choice of the particular ribozyme sequence. A subset of validated sequences, which uniformly span the range, are provided in Table 4.

TABLE 4

Activity data and sequences for the graded ribozyme set.

| Loop I | Loop II | µ (Validation) | N | Note |
|---|---|---|---|---|
| TGTGCTT | GTGA | 0.067 [0.063, 0.071] | 5 | Native sTRSV |
| TATG | AGAA | 0.067 [0.065, 0.070] | 2 | |
| TGTT | ACTA | 0.116 [0.104, 0.127] | 5 | |
| TTGT | CATA | 0.176 [0.157, 0.189] | 5 | |
| GGCT | AGCT | 0.273 [0.247, 0.298] | 5 | |
| TGCA | CGTT | 0.497 [0.454, 0.533] | 5 | |

TABLE 4-continued

Activity data and sequences for the graded ribozyme set.

| Loop I | Loop II | μ (Validation) | N | Note |
|---|---|---|---|---|
| CAGG | AGTT | 0.860 [0.833, 0.897] | 5 | |
| TGCA | CGCG | 1.41 [1.27, 1.54] | 5 | |
| TGCT | GTGA | 5.16 [4.97, 5.35] | 2 | |
| TGTGCTT | GTGA | 4.91 [4.70, 5.35] | 5 | sTRSVctl (scrambled catalytic core not shown) |

Figure 9:
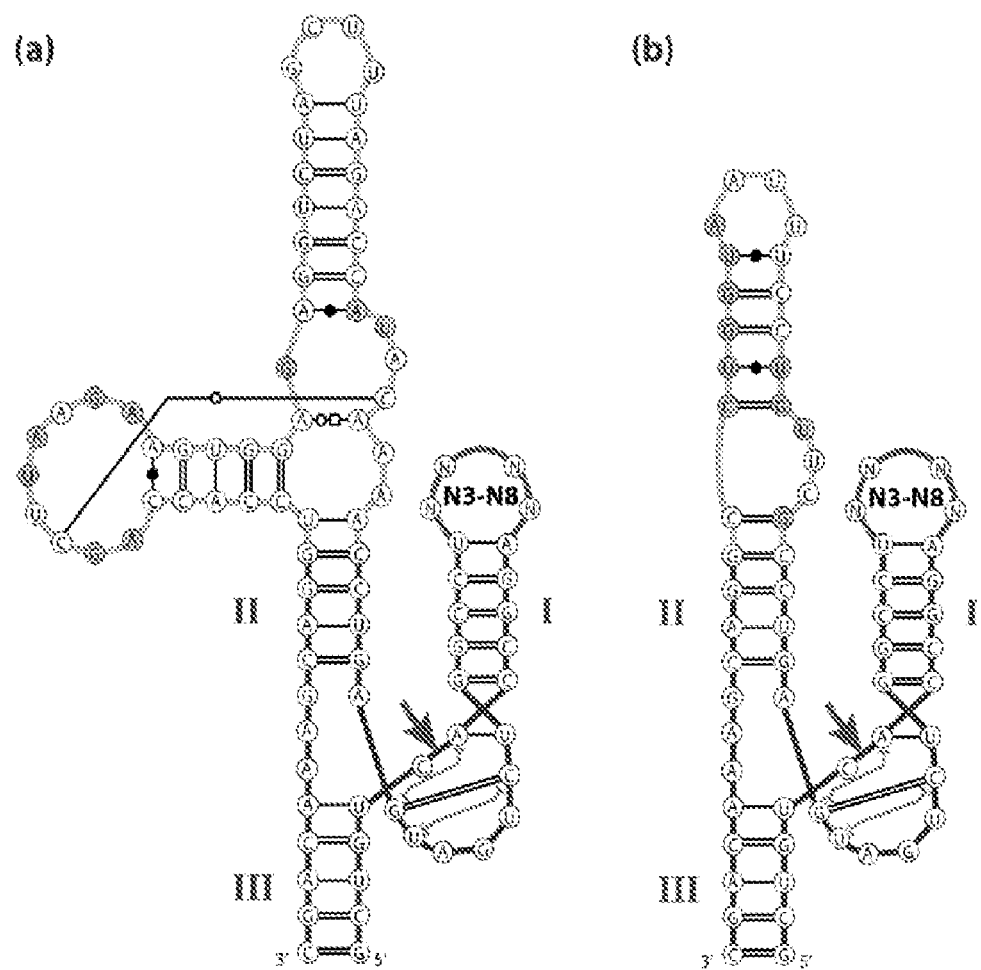
FIG. 9 Library design for tetracycline- and neomycin-responsive tertiary interaction switches. Shown are loop libraries (N3-N8; green) grafted onto stem II of the sTRSV hammerhead ribozyme (blue), with the tetracycline aptamer (a, gold) and neomycin (b, gold) aptamer on the opposing loop. The libraries also contain the aptamers grafted onto stem I (not shown). Red arrow indicates the ribozyme cleavage site in the backbone. Notation of interactions in the ribozyme and aptamers follow Leontis-Westhof notation[3] with the addition of green "I-beams" showing non-adjacent base-stacking interactions. Nucleotides in contact with the ligand are indicated in green. Interactions were based on 3D structures from the RCSB PDB entries 2QUS (ribozyme), 2KXM (neomycin aptamer), and 3EGZ (tetracycline aptamer). Base pair interactions were extracted from the PDB entries using FR3D. The sequence depicted in (a) is SEQ ID NO: 24 and the sequence depicted in (b) is SEQ ID NO: 25.

Extension of the tertiary interaction RNA device architecture and FACS-Seq strategy was explored as a general method for generating highly functioning gene-regulatory switches. Utilizing the same general architecture, we designed libraries for aptamers to neomycin and tetracycline, where the aptamer sequences were placed on either loop I or II of the ribozyme and a library of all possible sequences ranging in length from three to eight nucleotides was placed on the opposite loop (FIG. 9), requiring a library size of 174,720 sequences for each aptamer. To analyze the in vivo gene-regulatory activities of every library member, the FACS-Seq method was performed on these libraries as previously described.

The resulting NGS data were analyzed as previously described. The activity trends of the neomycin and tetracycline libraries exhibited notable differences from those observed for the theophylline libraries. Members of the tetracycline aptamer library displayed similar activity distributions; however, a smaller fraction of the sequences exhibited low μ values in the absence of ligand (FIG. 4a). The median μ was 0.28 in the absence of tetracycline for both replicates and 0.46 and 0.53 in the presence of tetracycline for the replicates. In contrast, the sequences from the neomycin library showed negligible reduction in the median μ in the absence of ligand (FIG. 4b). The neomycin library exhibited a median μ of 0.58 and 0.55 in the absence of neomycin and 0.57 and 0.55 in the presence of neomycin for the replicates. The data indicated that few of the sequences in the neomycin library exhibit a reduction in GFP levels, and thus self-cleaving activity. The low number of sequences exhibiting cleavage activity may be due to the design of the neomycin library (FIG. 9), which incorporated one extra base pair in the stem harboring the aptamer than the theophylline library.

NGS data was from these libraries to identify highly functional gene-regulatory switches responsive to tetracycline and neomycin. Five sequences were identified from the tetracycline aptamer library and four sequences from the neomycin aptamer library, that exhibit the largest switching ratios (Table 1) to validate. While the vast majority of sequences in the neomycin library, reduction in GFP levels or response to ligand was not observed (FIG. 4b), rare sequences that exhibit switching activity were identified. These selected RNA devices were individually reconstructed as previously described and assayed via flow cytometry (FIG. 4c, d). The μ values obtained through the flow cytometry analysis were compared with the μ values obtained from the FACS-Seq analysis. The best switches exhibited activation ratios of 9.1 for tetracycline and 6.5 for neomycin (FIG. 4c, d).

Example 4

Identifying Aptamer-Loop Consensus Sequences

The datasets obtained through the FACS-Seq analysis of the HHRz aptamer libraries were analyzed to identify consensus loop sequences that pair with different aptamers on the opposing loop and result in functional switches. Such consensus loop sequences provide additional support for particular interactions occurring between the modified loops. Starting with the theophylline AAG-variant on loop I and an eight-nt random loop II, we successively fixed one of the nucleotides on loop II and computed the $10^{th}$-percentile μ over the measured sequences with that particular nucleotide identity. The computed $10^{th}$-percentile μ ranged from 0.17 (loop II=CNNNNNNN) to 0.33 (loop II=NNNNNNNC). Similarly, we examined the effect of nucleotide identity pairwise by computing the μ for each of the 896 possible combinations and found $10^{th}$-percentile μ values ranging from 0.08 (CANNNNNN) to 0.37 (NCNNNNGN). We used these results to select the "best" consensus (lowest $10^{th}$-percentile μ; CNNNNNNN) and repeated the analysis on the remaining nucleotides to determine a consensus of CANNNNNN. Continuing this process, we arrived at an overall consensus sequence of CANNNAN for loop II with a $10^{th}$-percentile μ of 0.06; 4-fold lower than the $10^{th}$-percentile μ for the entire library of 0.24. Similarly, for the CAG-variant theophylline aptamer on loop I we identified a consensus sequence of NANNNNAA for loop II ($10^{th}$-percentile μ of 0.04, 5-fold lower than the $10^{th}$-percentile of 0.22 for the library). The consensus sequences for the other aptamers also exhibit an improvement over the full library, ranging between 1.2- and 3.0-fold (Table 5). The results provide support for particular interactions occurring between the aptamer sequence and modified loop sequence restoring ribozyme cleavage activity.

TABLE 5

GFP/mCherry values for consensus sequences identified for each aptamer tested.

| Aptamer | Loop integration | Median µ of library | 10$^{th}$-percentile µ of library | Consensus | 10$^{th}$-percentile µ of consensus |
|---|---|---|---|---|---|
| Theophylline (AAG) | I | 0.58 | 0.24 | CANNNNAN | 0.06 |
| Theophylline (CAG) | I | 0.66 | 0.22 | NANNNNNAA | 0.04 |
| Theophylline (AAG) | II | 0.45 | 0.24 | NGNANANN | 0.16 |
| Theophylline (CAG) | II | 0.57 | 0.24 | ACUNNNNN | 0.09 |
| Neomycin | I | 0.54 | 0.29 | NNNNNNNC | 0.25 |
| Neomycin | II | 0.52 | 0.38 | NNNNNNCN | 0.29 |
| Tetracycline | I | 0.36 | 0.25 | NNNNNNCN | 0.13 |
| Tetracycline | II | 0.33 | 0.06 | GNNUNNNA | 0.02 |

Median and 10$^{th}$-percentile GFP/mCherry (µ) is reported over all measured eight-nucleotide randomized library sequences for the opposing loop. Consensus sequences represent the lowest median µ identified during successive consensus minimization analyses.

Example 5

Figure 11:
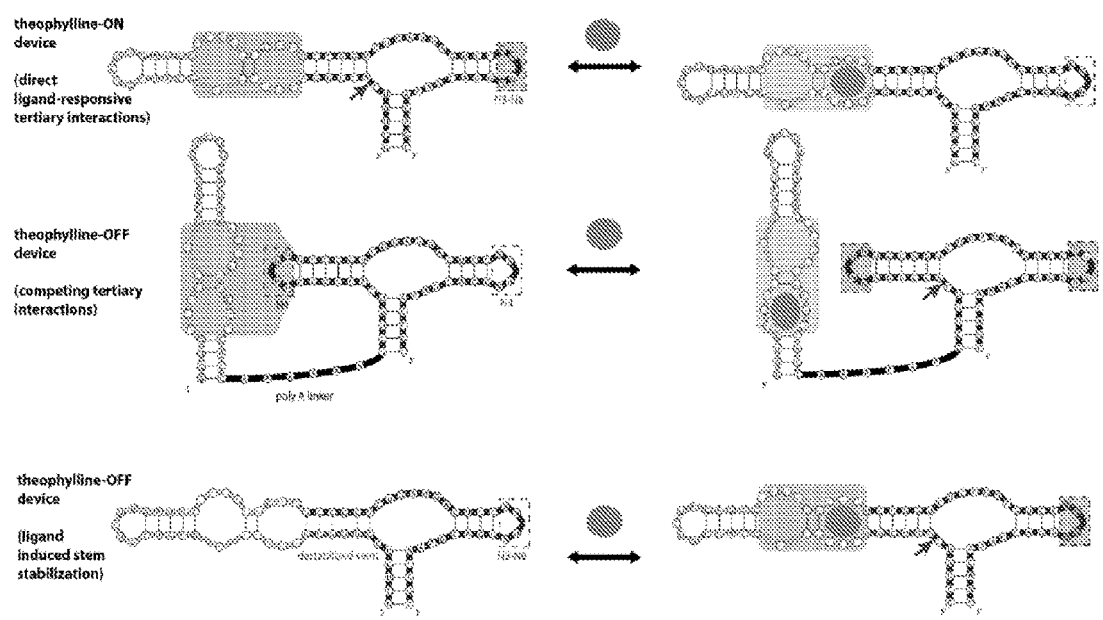
FIG. 11 shows alternative OFF-switch architectures for ligand-responsive ribozyme tertiary interactions. The sequence depicted in the structure at the top of the figure is SEQ ID NO: 26; at the middle of the figure is SEQ ID NO: 27; and at the bottom of the figure is SEQ ID NO: 28.

Strategies for Generating 'OFF-Switching' Ligand-Responsive Tertiary Interactions The tertiary switch architecture and screening platform for ON-switches (i.e., ribozymes that are autocatalyically inactive only in the presence of ligand) should also be capable of generating OFF-switches (i.e., ribozymes that are autocatalyically active only in the presence of ligand). OFF-switch only strategies similarly rely on our ability to engineer (select) ligand-responsive hammerhead ribozyme (HHRz) interactions (middle and bottom). FIG. 11 shows the tertiary interaction-modulating RNA device setup. Bases involved in tertiary interactions are in brown/gray, those involved in binding the (example theophylline) aptamer are in blue.

The direct ligand-responsive tertiary interaction architecture (FIG. 11, top) facilitates the generation of OFF-switches, in which a designed/selected HHRz loop sequence (grey boxed; N3-N8) only forms HHRz cleavage-mediating tertiary interactions with the aptamer loop upon aptamer-ligand binding. Tertiary interactions may be formed between the HHRz loop and the ligand-bound structure of the aptamer and/or the ligand molecule itself.

Alternatively, in a 'competing tertiary interactions' architecture (FIG. 11, bottom), the theophylline aptamer is connected via a poly A linker to the upstream (or downstream) HHRz. Both loops are (N4) randomized, with the expectation that the cleavage-inducing tertiary interactions are disrupted in the absence of ligand binding by tertiary interactions between one of the loops and the aptamer binding pocket. In the presence of ligand, the HHRz loop-to-aptamer tertiary interactions are disrupted and HHRz cleavage tertiary interactions are formed. This poly A linker has been extensively used in engineering of the hairpin ribozyme (see, e.g., Ivanov et al, 2005, FEBS—PMID: 16128815), between two helical-bulge domains forming the catalytic tertiary interactions. The ON-device sort results justify that one can sort for tertiary interactions between a HHRz tetraloop and the aptamer binding domain.

Lastly, a design strategy to generate OFF-switches with ligand-induced HHRz stem stabilization is also proposed. Using the same direct ligand-responsive tertiary interaction architecture (FIG. 11, top), one can rationally design or screen HHRz loop libraries (loop II here; N3-N8) for sequences that efficiency cleave both in presence and absence of ligand (i.e. hammerhead ribozymes with an aptamer loop that are ligand unresponsive). The HHRz stem sequence connecting the HHRz core and aptamer loop can then be destabilized by tuning the strength of the Watson Crick base-pairing (and mispairing), such that the stem is only formed in the presence of ligand, stabilized by ligand-aptamer binding. This type of stabilization approach to switch design was developed and validated for minimal HHRz that have in vitro functionality only (Soukup & Breaker, 1999, Structure—PMID: 10425680). Our new designs that generate tertiary interactions between aptamer loop and HHRz loop, facilitate the generation of in vivo functioning switches utilizing ligand-induced HHRz stem stabilization.

Methods

Tertiary Interaction RNA Switch Library Design

Tertiary interaction switch libraries were constructed based on the sequence of the tobacco ringspot virus (sTRSV) HHRz by replacing either the wild-type loop I or II sequences with previously identified minimal aptamer sequences and the other loop with a randomized sequence between three and eight nucleotides (Table 2). This library design resulted in 174,720 distinct sequences for each aptamer. The aptamer sequences have a structurally conserved terminal helix that is reconstituted by a ribozyme stem in our design architecture (FIG. 1c). The TCT8-4 theophylline aptamer sequence and also a variant sequence with a single base change (C28A, in the postulated binding pocket of the aptamer) were used with the terminal stem removed. The first base pair of the terminal stems of the tetracycline and neomycin aptamer were retained in the device design as it has been shown to be important to ligand binding (FIG. 9b). Each of the switches was flanked by a spacer sequence designed to minimize interactions between the surrounding sequences and the switch sequence.

Library Construction and High-Efficiency Yeast Transformation

All RNA device libraries were assembled from two oligonucleotide fragments through overlap-extension PCR using PFU Ultra II HS DNA polymerase (Agilent Technologies). The fragments were designed to overlap in the region between the two stems, allowing the random loop regions to be modularly coupled with the four aptamer sequences (Table 2). The resulting sequences were combined into three distinct libraries based on the target ligand. In preparation for yeast-mediated gap-repair cloning, each DNA library was amplified by PCR (PFU Ultra II HS; Agilent) with primers (Table 2) with overhangs homologous to portions of a previously described two-color screening plasmid (pCS1748). The low-copy plasmid backbone is designed to place the switches in the 3' UTR of a GFP reporter gene, and also harbors a separate mCherry expression cassette.

Briefly, for each of the three libraries, 50 ml yeast culture ($OD_{600}$ 1.3-1.5) was incubated with Tris-DTT buffer (2.5 M DTT, 1 M Tris, pH 8.0) for 15 min at 30° C., pelleted, washed, and resuspended in Buffer E (10 mM Tris, pH 7.5, 2 mM $MgCl_2$) to 300 μl. To 50 μl of the yeast cell suspension, 2 μg of linearized plasmid and 1 μg of library insert DNA was added and the DNA-cell suspension was electroporated (2 mm gap cuvette, 540 V, 25 μF, 1000Ω). Transformed cells were diluted to 1 ml volume in yeast peptone dextrose (YPD) media, incubated for 1 hr, then further diluted in selective media (synthetic complete media with a uracil dropout solution containing 2% dextrose; SC-URA) and propagated for FACS screening[13]. Each of the libraries was independently transformed into yeast twice providing two biological replicates (or six library samples in total), which were handled separately through all subsequent steps of the FACS-Seq method. The budding yeast strain W303a (MATα leu2-3,112 trp1-1 can1-100 ura3-1 ade2-1 his3-11,15) was used in all experiments. All fungal growth and propagation steps were carried out in a 30° C. incubator, shaking at 230 rpm, unless otherwise stated.

Library Prescreening for Active Ribozyme Sequences

Following high-efficiency transformation and subsequent cell growth, the six samples were prescreened through FACS to enrich for cells that exhibit reduced GFP expression or by extension ribozyme cleavage activity in the absence of ligand. Cells harboring the libraries were back-diluted 20:1 to an approximate $OD_{600}$ of 0.07 in SC-URA media and grown for 6 hrs to $OD_{600}$~0.8. Cells were washed, resuspended in PBS (Life Technologies) with 1% BSA (Sigma-Aldrich), stained with DAPI viability dye (Life Technologies), then filtered through a 40 μm cell strainer (BD Biosciences) prior to analysis on a FACSAria II cell sorter (BD Biosciences).

GFP was excited at 488 nm and measured with a splitter of 505 nm and bandpass filter of 525/50 nm. mCherry was excited at 532 nm and measured with a splitter of 600 nm and bandpass filter of 610/20 nm. Fluorescence levels of cells harboring a negative-control plasmid (pCS4) were used to determine background, autofluorescence levels of both colors. Initial gates based on the forward scatter area, side scatter area, side scatter height, and side scatter width were used to gate out cell debris and non-viable cells. Next, a gate which removed cells with mCherry levels comparable to the no-color control was applied (~15% of cells removed), followed by a gate which removed any cells with GFP levels that saturated the instrument measurement (~2% of cells removed). Finally, a gate based on the ratio of GFP to mCherry expression (μ) established to collect cells with a μ below a threshold value. This threshold was set such that ~10% cells that passed the parent gates were collected. The final sort gate was applied to enough cells to ensure at least 15 cells per library sequence were considered. The actual counts of cells sorted and collected.

Sorting of RNA Device Libraries into Activity Bins

The prescreened cell populations were grown for 14.5 hrs at 30° C. in SC-URA, after which cell counts were measured using a MACSQuant VYB flow cytometer (Miltenyi Biotec GmbH). The six samples were then normalized to $3.1 \times 10^6$ cells/ml by addition of media, and growth was continued for 12 hrs under the same conditions, after which they were back-diluted 100:1 to $OD_{600}$~0.05 and grown an additional 7 hrs to $OD_{600}$~1.3 keeping them in the exponential growth phase throughout. In parallel to the above, a separate culture of cells, which contained a set of four graded ribozymes in approximately equal ratio, was similarly transformed and grown. This reference culture was kept separate for use in setting the final gating, as described below. Each of these six cultures was back-diluted 20:1 into two separate 50 ml samples of fresh media to an $OD_{600}$~0.07, with the target molecule added to one of the two samples. The target molecules were added to the following final concentrations: theophylline 5 mM, neomycin 0.1 mM, and tetracycline 1 mM. The cultures were grown for 6 hrs at 30° C. to $OD_{600}$~0.8 to ~1.0.

The yeast cultures were spun down and resuspended in PBS (Life Technologies) to a final concentration of $2 \times 10^7$ cells/ml. The twelve samples were then combined into four mixtures prior to sorting; 1– (replicate 1, no target), 1+ (replicate 1, with target), 2– (replicate 2, no target), 2+ (replicate 2, with target). The sequence differences between the aptamers would allow for the three combined samples to be resolved during subsequent NGS processing, while reducing the number of samples to sort.

Sorting of the samples into activity bins was performed on a FACSAria II Cell Sorter (BD Biosciences). Excitation and emission filters for GFP and mCherry and scatter gating were as described above. In addition, a viability gate based on DAPI and side-scatter area was applied to exclude the DAPI-positive dead cells from subsequent analysis. DAPI was excited at 355 nm and measured with a bandpass filter of 450/50 nm. The cells that passed these gates were then divided into one of eight gates based on the GFP/mCherry ratio to allow binned sorting of the cells. The gates were set using the reference culture of four graded ribozymes. These ribozymes were chosen to have GFP/mCherry levels that uniformly span the range of interest. Gate edges between bins 1&2, 3&4, 5&6, and 7&8 were set on the log(GFP) vs. log(mCherry) display to equally split the populations for each of these graded ribozymes. The remaining three bin edges (i.e., between bins 2&3, 4&5, 6&7) were then set to approximately halfway between each of these. Since the sorter has a maximum capability of four-way sorting, the samples were each sorted twice based on the defined gates. Cells falling into bins 1-4 were collected in the first sort and all other cells were discarded. In the second sort, cells falling into bins 5-8 were collected. SC-URA at a volume (3 ml) of at least 3:1 was added to each collection tube immediately after sorting. Sorting of each sample, except 2+, was continued until at least ~6 million cells were collected. The following number of cells were collected over the eight bins for each sample over a 2.5 hr period: 1− 7.6 million, 1+ 7.1 million, 2− 7.1 million, and 2+ 5.9 million.

NGS Sample Preparation

Sorted samples were grown in SC-URA at 30° C. for up to 32 hrs, with samples stored at 4° C. once they reached $OD_{600}$~0.7. The volumes for each culture were chosen such that each sample contained at least 50× the number of cells that were initially sorted into that bin. In addition to these 32 cultures, seven additional cultures were processed in parallel. These were cultures taken prior to the prescreening (the three target libraries pooled in each of the two replicates), just prior to the main sort (four samples of pooled target libraries), and a culture of cells containing an unmodified plasmid (no switch inserted) as a negative control. Cells from each of these 39 samples were collected, lysed, and the DNA from each sample was extracted using the ZR Fungal/Bacterial DNA MiniPrep™ (Zymo Research), according to the manufacturer's instructions. A diversity control was then added to each sample of prepared DNA. This control consisted of a 17-nt random region of DNA (synthesized using a machine mix of the four nucleotides) flanked by the spacer sequence used with the switch sequences. Since almost every molecule of this control has a unique sequence, subsequent occurrence counting of each distinct sequence within the control was used to compute the mean number of reads due to any single molecule that existed in the sample at this point. This method was used to verify that all bins had less than 1.25 reads/molecule with most less than 1.05 read/molecules.

The DNA encoding the RNA devices was amplified from the bulk DNA in each sample through 14 cycles of PCR using PFU Ultra II HS (Agilent Technologies) and 400 nM primers based on the spacer sequences (T7_W_Primer, X_Primer-RC; Table 2). Each reaction was sized such that the number of molecules in the template was at least 10× the number of NGS reads planned for that sample, while keeping the template volume at or below 25% of the total PCR volume. The PCR products for each bin were used as the template for a second PCR, which used primers with overhang regions corresponding to the standard Illumina adapter sequences. DNA barcodes were also added to allow identification of the particular sample from the NGS reads. These barcodes are a sequence of up to seven nucleotides that were added to each end of the sequence of interest. The variable length also increased base diversity at each read position, which can improve read quality during Illumina sequencing. In addition to the 39 samples from the DNA extractions, an individually barcoded sample containing an equimolar mix of the original DNA libraries used for the transformations was also included as a control to verify the pre-transformation library distribution.

Samples were quantified on a Bioanalyzer 2100 (Agilent Technologies) and sequenced on an Illumina HiSeq 2500 by Elim Biopharmaceuticals, Inc. using 2×100 paired-end reads. The sample was run using Illumina standard procedures, with PhiX (Illumina) added (to 15% by molarity) to further increase diversity at nucleotide positions which would, otherwise, have a significant fraction of the sample sharing the same base call and result in lower read quality.

NGS Data Processing

The paired-end reads were first joined using PEAR. The joined sequences were then split using the concatenated barcodes on each end into 40 separate files corresponding to the 32 bins (2 conditions×8 bins×2 replicates) plus 8 control samples consisting of the DNA library, post-transformation plasmid prep (2 replicates, each pooling the three libraries), pre-sort plasmid prep (2 replicates×2 conditions), and a blank plasmid prep (cells with the parent plasmid, no switch integrated; controls for cross-contamination). Sequences without an exact match to expected barcodes, spacer, and library entry sequences were ignored during the main analyses, although the full set of sequences was used for assessing controls. The matching data (46.7M reads) were then collapsed into tables that gave the count of occurrences of each designed sequence for each bin or control sample.

Prior to beginning the main FACS-Seq experiment, we collected flow cytometry data on cells harboring the two-color expression constructs that incorporate four graded ribozymes that span the expression range of interest. Analysis of these data and prior cytometry on cells harboring a single switch sequence incorporated into the expression construct indicate that the GFP/mCherry ratio follows a log-normal distribution with a uniform variance over a wide range of ratios as is often the case for biological quantities. The observed coefficient of variation for these samples was measured to be 0.31. Based on this observation, a method was developed for estimating the underlying mean GFP/mCherry ratio of a population of cells from the binned cell counts with a resolution better than the bin width, limited only by the model mismatch and the number of cells counted.

Sequencing results were separated by barcode and sequence identity to produce a histogram of read counts, $r_{i,b}$, per sequence, i, in each of the eight FACS bins, b. The read counts were then normalized by a factor $C_b/R_b$, where $C_b$ is the total number of cells sorted in bin b and $R_b$ is the total number of NGS reads with barcode corresponding to bin b, to give an estimate of cells per bin, $c_{i,b}$. This accounts for the differences between the bins in post-sort growth, plasmid preparation, or NGS mixing. The average number of cells per read for each bin over each of the samples was calculated. With the GFP/mCherry fluorescence ratios, $A_{b,b+1}$, used to set the FACS gates between bins b and b+1, the $c_{i,b}$ were fit to a model that assumes that these ratios are random variables that follow a log-normal distribution with a constant variance of 0.3. That is, we assumed:

$$c_{i,b} = \begin{cases} C_i \int_{\log A_{b-1,b}}^{\infty} N(x, \log a_i, \sigma) dx & b = 8 \\ C_i \int_{\log A_{b-1,b}}^{\log A_{b,b+1}} N(x, \log a_i, \sigma) dx & 2 \leq b \leq 7 \\ C_i \int_{-\infty}^{\log A_{b,b+1}} N(x, \log a_i, \sigma) dx & b = 1 \end{cases}$$

where $N(x,\mu,\sigma)$ is the normal probability density function with mean $\mu$, variance $\sigma^2$, evaluated at x, $C_i = \Sigma c_{i,b}$, b=0 . . . 8 and $\sigma$=0.30 (CV=0.31).

The fits were performed using custom MATLAB (MathWorks) code available at http://github.com/btownshend/TwoColor. These fits resulted in an estimate for each sequence, $a_i$, of the GFP/mCherry ratio for that sequence. The method can also produce confidence intervals for $\mu$ based on the bin statistics, but this captures only the variability due to counting statistics of the reads, $r_{i,b}$, and does not model systematic variability in $\sigma$ or $\mu$ such as post-sort growth bias or model mismatch. We also determined error bounds on each of these calculated values based on the difference between the two biological replicates and found that these were in agreement with the model confidence intervals with approximately 80% of the replicate $\mu$ values falling within the 80% confidence intervals.

Identification of Switches

Potential switches sensitive to each of the target molecules were identified by analysis of the μ values in the −target and +target conditions. For the theophylline aptamers, sequences were considered that satisfied the following constraints, with the two replicates combined: at least 20 cells measured, $\mu_{-target}<0.10$, $\mu_{+target}>0.50$ (FIG. 2b). These values were chosen to identify switches with activation ratios of at least 5 fold and gene expression levels in the absence of ligand close to that of the wild-type sTRSV ribozyme. Of the 205 sequences that satisfied these constraints, seventeen representative sequences were selected for validation. Similarly, for the tetracycline aptamer, sequences were considered that had at least 40 cells measured, $\mu_{-target}<0.025$, $\mu_{+target}>0.25$. These criteria were satisfied by seventeen sequences of which five were selected for further validation. For the neomycin aptamer, fewer sequences exhibited strong switching so the criteria were relaxed: $\mu_{-target}<0.15$, $\mu_{+target}>0.25$ over at least 40 cell measurements, resulting in seven hits with four selected for further validation.

Flow Cytometry Validation of Reconstructed Sequences

Specific switch sequences were synthesized from overlapping oligonucleotides using overlap-extension PCR as described for the device library constructions. These were gap-repair transformed into the yeast two-color screening plasmid along with control plasmids by the lithium acetate/single-stranded carrier DNA/polyethylene glycol method, with each switch sequence verified using Sanger sequencing. At least three individual colonies were picked and inoculated in SC-URA media. Cultures were grown overnight, back-diluted 20:1 to an $OD_{600}$~0.07 and then grown 6 hrs in the absence and presence of a ligand target, at the same ligand concentrations as used for the FACS-Seq assays. The cells were then spun down and resuspended in an equal volume of 1×PBS buffer (Life Technologies) with 1% BSA (Fraction V, EMD Millipore) and a DAPI viability dye (Life Technologies). GFP was excited at 488 nm and measured with a bandpass filter of 525/50 nm. mCherry was excited at 561 nm and measured with a bandpass filter of 615/20 nm. DAPI was excited at 405 nm and measured with a bandpass filter of 450/50 nm. Prior to each use, voltages of fluorescence PMT detectors were calibrated with MACSQuant calibration beads to fix GFP and mCherry levels. For each culture, 10 μl of sample was analyzed, which captured 50,000-150,000 events while also providing cell density measurements. The data was analyzed using a custom MATLAB program to gate for mCherry expression above the no-color controls and non-saturating values for GFP and mCherry, and then extract μ, the median GFP/mCherry ratio. Since cultures that contain tetracycline produce non-specific fluorescence in the GFP emission region, the μ values for this condition were corrected by subtracting a fixed offset. This offset, 0.17, was determined from the mean difference in the plus and minus-tetracycline conditions for control samples with an "mCherry-only" plasmid that did not contain a GFP gene.

Note that the NGS data is based on cells sorted through a FACSAria II Cell Sorter. An in-house flow cytometer (Miltenyi Biotec MACSQuant VYB) was used for validation measurements. The GFP and mCherry levels are given in arbitrary fluorescence units that differ between the two instruments, but in all cases are treated as a linear function of the actual protein levels in order to compute μ. Thus, the μ values from the validation and the NGS data each incorporate a different linear scale factor.

Surface Plasmon Resonance Validation of Reconstructed Sequences

Representative FACS-Seq sort identified theophylline-responsive RNA device cleavage kinetics and ligand sensitivity were determined by surface plasmon resonance (SPR), using previously described protocols. Briefly, the RNA device DNA templates were amplified by PCR (PFU Ultrall HS; Agilent) with primers containing overhangs corresponding to the T7 RNAP promoter and cis-blocking sequences that prevent device cleavage during in vitro T7 transcription (Table 2; SPR templates). A second PCR (KAPA HiFi PCR Kit; Kapa Biosystems) with short primers was performed to enrich the product for full-length sequences (Table 2; SPR_fwd_primer, SPR_rev_primer). A total of 100-200 ng of PCR product was transcribed in a 50 μl reaction, consisting of the following components: 1×RNA Pol Reaction Buffer (New England Biolabs), 2.5 mM of each rNTP, 2 μl Superase•In (Life Technologies), an additional 4 mM $MgCl_2$ (Ambion), 2 μl T7 RNA Polymerase (New England Biolabs). After incubation at 37° C. for 2 hrs, the transcription reaction was purified with the RNA Clean and Concentrator™-25 kit (Zymo Research) according to the manufacturer's instructions and estimated by Nanodrop.

The Biacore X100 sensor chip (GE Healthcare) surface immobilized with DNA activator was generated as previously described. The Biacore X100 instrument (GE Healthcare) was equilibrated with the physiologically-relevant reaction buffer at 25° C. prior to all ribozyme cleavage assays. The SPR baseline was stabilized by performing 2-5 startup cycles, where each cycle includes a capture and a regeneration step. The capture step was performed by an injection of a total of 10-25 ng transcribed cis-blocked RNA diluted in HBS-N (GE Healthcare) buffer over the reaction flow cell (FC2) for 1 min at a flow rate of 10 μl/min. The capture step typically yielded ~50-700 RU of the SPR signal for the described constructs. The regeneration step was performed by an injection of 25 mM NaOH over both flow cells for 30 s at a flow rate of 30 μl/min. Following the startup cycles, assay cycles were performed. Each assay cycle includes a capture, a reaction, and a regeneration step. The capture and regeneration steps in an assay cycle were performed as described for those in the startup cycle. The reaction step was performed by an injection of the running buffer containing 500 μM $MgCl_2$ with or without theophylline over both FCs for 300-500 s at a flow rate of 10 Biacore sensorgram processing and analysis were performed using custom Matlab software. Due to the slight time delay at which injected analyte reaches the respective flow cells, the resultant sharp spikes at the beginning and the end of injection were excluded from the analysis. The processed sensorgram (R) was fit to a simple exponential equation $R=R_0[f_c e^{-k_d t}+1-f_c]$, where $R_0$ (fit locally for each replicate) is the initial SPR signal before the cleavage reaction, $f_c$ (fit globally for a given RNA sample) is the extrapolated residual response at the end of the cleavage reaction as a fraction of the captured RNA signal, and $k_d$ is the first-order RNA cleavage (dissociation) rate constant. Reported values are the mean of at least three independent experiments.

SPR-based cleavage assays were performed at various theophylline concentrations to generate dose-response curves. The RNA dissociation rate constant ($k_d$) at each theophylline concentration ([theo]) was fit to the sigmoidal equation $k_d=k_{d,min}+(k_{d,max})/(1+[theo]/IC50)$ using MATLAB, where $k_{d,max}$ and $k_{d,min}$ are the maximum and minimum RNA dissociation rate constants, evaluated in absence of and with the highest theophylline concentration assayed, respectively. The $IC_{50}$ here is defined as the theophylline concentration at which $k_d$ is halfway between the minimum and maximum values. Replicate dose response measurements were fit to the three parameter logistic equation, with a shared $k_{d,max}$, and $k_{d,min}$, and $IC_{50}$ for all replicate assays for a given device.

The binding affinities of the CAG- and AAG-variant theophylline aptamers were determined at the same conditions as the SPR-based cleavage assay (500 µM $MgCl_2$, 150 mM NaCl and 10 mM HEPES (pH 7.4), at 25° C.) using a previously described SPR-based binding assay[47]. Aptamer equilibrium dissociation constants ($K_D$) were determined from fit of binding responses to theophylline, measured at concentrations spanning four orders of magnitude, to a steady-state affinity model using MATLAB.

Consensus Analyses

Analyses of NGS data for consensus sequences were performed using custom MATLAB software. For each possible identity of one nucleotide, or pair of identities for two nucleotides, the $10^{th}$ percentile of µ was formed over all sequences that match that nucleotide or nucleotides. In this way, sequence positions that can result in low µ values are found without being overly sensitive to the sequences, which may, due to the effects of other sequence positions, have a much higher µ. Raw NGS data was pooled from the two biological replicates and only sequences for which we have at least 20 cells sorted were used in the computations. Initially all degenerate loop nucleotides were allowed to vary. After computing each stage, the nucleotide position with the greatest effect on the average was fixed at the value that gave the lowest average µ, and the process was repeated four times. The reported consensus sequence is the last of these with at least 100 sequences used in the averaging.

Discussion

RNA folding is largely hierarchical and an ensemble of tertiary structures are formed for each secondary structure. Secondary structure switching mechanisms are believed to exhibit significant misfoldings and/or conformation interconversion timescales that restrict switching activity and thus gene silencing efficacy. In contrast, the tertiary interaction switches adopt one secondary structure conformation, with aptamer and ribozyme secondary structures preformed, enabling the interactions involved in ligand-binding and ribozyme cleavage to directly compete to determine the ON and OFF states. In support of this hypothesis, in vitro cleavage assays indicated that the cleavage kinetics of the tertiary interaction switches, unlike the secondary-structure switching devices, are completely inhibited at high ligand concentrations. In addition, the ligand sensitivities of the tertiary interaction switches ($IC_{50}$ 2.4-4.2 µM) unlike the secondary-structure switching devices are near the equilibrium dissociation constant of the initial theophylline aptamers measured under the assay conditions ($K_D$ 2.4-4.4 µM), suggesting that ligand binding is directly competing with cleavage activity.

Our methodology, comprising a novel device framework and FACS-Seq strategy, provides a framework for efficiently generating tertiary interaction devices with design-level modularity rather than sequence-level modularity. The broader application of our approach to diverse aptamer-ligand pairs is dependent on the ability to restore activity of a ribozyme that has one loop modified with an arbitrary sequence by generating an appropriate opposing loop sequence that restores tertiary interactions. The feasibility of this approach is supported by the loop sequence flexibility observed in our analysis of active sequences within a ribozyme library. The data generated through the FACS-Seq assay can be used to define consensus loop sequence requirements for activity with different aptamer sequences, thereby increasing our understanding of sequence-structure-function relationships.

The present tertiary switch framework is robust to aptamers of varying length and complexity and identifies solutions that current structure-guided design methods are unable to obtain. The massively parallel assay characterizes each member of large libraries under identical conditions providing extensive data for understanding sequence-structure-function relationships and a resource for improving computational models that attempt to predict these relationships.

A combination of binned FACS and NGS on libraries was used. The data analysis extends these methods by combining information about the distribution statistics of the measurements to produce maximum likelihood estimates of the activity of individual library members at a resolution better than the binning widths. Thus, the number of cells captured and sequenced rather than the bin widths, determine the resolution of the measurements. Our data indicate that these measurements are highly reproducible and are tightly predictive of subsequent single-sequence cytometry validation.

An efficient pipeline for engineering ligand-responsive ribozyme tertiary interactions to generate RNA devices is described. Also developed is a graded ribozyme library with gene-regulatory activities spanning a 77-fold range in vivo, thereby expanding the tools available for precisely controlling expression across diverse biological systems. The FACS-Seq approach supports parallel measurements of the activities of large RNA regulator libraries under chosen conditions. By assaying every member of these libraries in parallel within a single culture, this method enables elucidation of consensus sequences for genetic devices. The non-iterative method of combining existing aptamers, including those derived from naturally occurring riboswitches, with a ribozyme to build genetic sensors that outperform those currently available will advance our ability to develop sophisticated genetic tools and our understanding of the underlying sequence-structure-function relationships that empower rational design of complex biomolecules.

What is claimed is:

1. A ligand-responsive hammerhead ribozyme that, relative to a wild-type hammerhead ribozyme, comprises
   i. a first loop that has been replaced by an RNA aptamer that binds to a ligand, and
   ii. a second loop, wherein
   the first and second loops are loops L1 and L2 respectively, or loops L2 and L1 respectively, and
   the aptamer and the second loop interact in a ligand-dependent manner and autocatalytic cleavage of the ribozyme is ligand-responsive.

2. The ribozyme of claim 1, wherein the first loop is loop L1 and the second loop is loop L2.

3. The ribozyme of claim 1, wherein the first loop is loop L2 and the second loop is loop L1.

4. The ribozyme of claim 1, wherein the ribozyme is a Type III hammerhead ribozyme.

5. The ribozyme of claim 1, wherein binding of the ligand to the aptamer causes the first and second loops to disassociate from one another, thereby inhibiting autocatalytic cleavage of the ribozyme.

6. The ribozyme of claim 1, wherein binding of the ligand to the aptamer causes the first and second loops to interact with one another, thereby activating autocatalytic cleavage activity of the ribozyme.

7. The ribozyme of claim 1, wherein the aptamer is at least 20 nucleotides in length.

8. The ribozyme of claim 1, wherein the ligand for the aptamer has a molecular weight of less than 1 kDa.

9. The ribozyme of claim 1, wherein the aptamer is directly connected to a stem region of the ribozyme.

10. The ribozyme of claim 1, wherein the ribozyme comprises:
    a first stem of 4-7 bp;
    a second stem of 4-6 bp;
    a third stem of 3-6 bp;
    wherein: (i) the first and second stems are joined by sequence CUGANGA, (ii) the second and third stems are joined by sequence GAAA, and (iii) the second and third stems are joined by sequence NUH;
    the first stem or the second stem is directly joined by an aptamer and the other of the first and second stems terminates in a loop that contains a modified sequence; and
    wherein the aptamer and the modified sequence interact in a ligand-dependent manner and autocatalytic cleavage of the ribozyme is ligand-responsive.

11. The ribozyme of claim 1, wherein the ribozyme comprises at least one non-naturally occurring nucleotide.

12. A construct comprising a nucleic acid encoding the ligand-responsive hammerhead of claim 1.

13. The construct of claim 12, wherein the nucleic acid is present in an expression cassette comprising: a promoter, a coding sequence, and a 3' UTR.

14. The construct of claim 12, wherein the nucleic acid is present in a 3' UTR of the expression cassette.

15. A cell comprising the construct of claim 12.

16. The cell of claim 15, wherein the cell is a eukaryotic cell.

17. A method for modulating expression of a gene comprising:
    contacting a cell of claim 15, with a ligand for the aptamer, thereby causing the first and second loops to associate or disassociate and modulating expression of the product encoded by the coding sequence.

18. The method of claim 17, wherein the product encoded by the coding sequence is a protein or a non-coding RNA.

19. The method of claim 17, wherein binding of the ligand to the aptamer inhibits autocatalytic cleavage of the ribozyme, thereby increasing expression of the protein encoded by the coding sequence.

20. The method of claim 17, wherein binding of the ligand to the aptamer induces autocatalytic cleavage of the ribozyme, thereby reducing expression of the protein encoded by the coding sequence.

* * * * *

SEQUENCE LISTING

```
<160> NUMBER OF SEQ ID NOS: 28

<210> SEQ ID NO 1
<211> LENGTH: 125
<212> TYPE: RNA
<213> ORGANISM: Artificial sequence.
<220> FEATURE:
<223> OTHER INFORMATION: Synthetic nucleic acid.

<400> SEQUENCE: 1
```

-continued aaacaaacaa agcugucacc ggaugugcuu uccggucuga ugaguccguu guccauacca    60
gcaucgucuu gaugcccuug gcagggacgg gacggaggac gaaacagcaa aaagaaaaau   120
aaaaa                                                              125

<210> SEQ ID NO 2
<211> LENGTH: 125
<212> TYPE: RNA
<213> ORGANISM: Artificial sequence.
<220> FEATURE:
<223> OTHER INFORMATION: Synthetic nucleic acid.

<400> SEQUENCE: 2
aaacaaacaa agcugucacc ggaaucaagg uccggucuga ugaguccguu guccauacca    60
gcaucgucuu gaugcccuug gcagggacgg gacggaggac gaaacagcaa aaagaaaaau   120
aaaaa                                                              125

<210> SEQ ID NO 3
<211> LENGTH: 125
<212> TYPE: RNA
<213> ORGANISM: Artificial sequence.
<220> FEATURE:
<223> OTHER INFORMATION: Synthetic nucleic acid.

<400> SEQUENCE: 3
aaacaaacaa agcugucacc ggaugugcuu uccggucuga ugaguccguu gaguauacca    60
gcaucgucuu gaugcccuug gcagacugua uacggaggac gaaacagcaa aaagaaaaau   120
aaaaa                                                              125

<210> SEQ ID NO 4
<211> LENGTH: 11
<212> TYPE: RNA
<213> ORGANISM: Artificial sequence.
<220> FEATURE:
<223> OTHER INFORMATION: Synthetic nucleic acid.

<400> SEQUENCE: 4
aaacaaacaa a                                                        11

<210> SEQ ID NO 5
<211> LENGTH: 17
<212> TYPE: RNA
<213> ORGANISM: Artificial sequence.
<220> FEATURE:
<223> OTHER INFORMATION: Synthetic nucleic acid.

<400> SEQUENCE: 5
aaaaagaaaa auaaaaa                                                  17

<210> SEQ ID NO 6
<211> LENGTH: 22
<212> TYPE: RNA
<213> ORGANISM: Artificial sequence.
<220> FEATURE:
<223> OTHER INFORMATION: Synthetic nucleic acid.

<400> SEQUENCE: 6
gggaaacaaa caaaguuguu uu                                            22

<210> SEQ ID NO 7
<211> LENGTH: 52
<212> TYPE: RNA

```
<213> ORGANISM: Artificial sequence.
<220> FEATURE:
<223> OTHER INFORMATION: Synthetic nucleic acid.

<400> SEQUENCE: 7
gcugucaccg gaugugcuuu ccggucugau gaguccguga ggacgaaaca gc          52

<210> SEQ ID NO 8
<211> LENGTH: 52
<212> TYPE: RNA
<213> ORGANISM: Artificial sequence.
<220> FEATURE:
<223> OTHER INFORMATION: Synthetic nucleic acid.

<400> SEQUENCE: 8
gcugucaccg gaugugcuuu ccgguacgug agguccguga ggacagaaca gc          52

<210> SEQ ID NO 9
<211> LENGTH: 30
<212> TYPE: RNA
<213> ORGANISM: Artificial sequence.
<220> FEATURE:
<223> OTHER INFORMATION: Synthetic nucleic acid.

<400> SEQUENCE: 9
auaccagcau cgucuugaug cccuuggcag                                   30

<210> SEQ ID NO 10
<211> LENGTH: 30
<212> TYPE: RNA
<213> ORGANISM: Artificial sequence.
<220> FEATURE:
<223> OTHER INFORMATION: Synthetic nucleic acid.

<400> SEQUENCE: 10
auaccagcau cgucuugaug cccuuggaag                                   30

<210> SEQ ID NO 11
<211> LENGTH: 19
<212> TYPE: RNA
<213> ORGANISM: Artificial sequence.
<220> FEATURE:
<223> OTHER INFORMATION: Synthetic nucleic acid.

<400> SEQUENCE: 11
gcuuguccuu uaauggucc                                               19

<210> SEQ ID NO 12
<211> LENGTH: 47
<212> TYPE: RNA
<213> ORGANISM: Artificial sequence.
<220> FEATURE:
<223> OTHER INFORMATION: Synthetic nucleic acid.

<400> SEQUENCE: 12
aaaacauacc agauuucgau cuggagaggu gaagaauucg accaccu                47

<210> SEQ ID NO 13
<211> LENGTH: 69
<212> TYPE: RNA
<213> ORGANISM: Artificial sequence.
<220> FEATURE:
<223> OTHER INFORMATION: Synthetic nucleic acid.

<400> SEQUENCE: 13
aaacaaacaa agcugucacc ggauccgguc ugaugagucc ggacgaaaca gcaaaaagaa  60
``` aaauaaaaa                                                               69

<210> SEQ ID NO 14
<211> LENGTH: 47
<212> TYPE: DNA
<213> ORGANISM: Artificial sequence.
<220> FEATURE:
<223> OTHER INFORMATION: Synthetic nucleic acid.

<400> SEQUENCE: 14
aatttaatac gactcactat agggaaacaa acaaagctgt caccgga                     47

<210> SEQ ID NO 15
<211> LENGTH: 29
<212> TYPE: DNA
<213> ORGANISM: Artificial sequence.
<220> FEATURE:
<223> OTHER INFORMATION: Synthetic nucleic acid.

<400> SEQUENCE: 15
tttttatttt tcttttgct gtttcgtcc                                          29

<210> SEQ ID NO 16
<211> LENGTH: 23
<212> TYPE: DNA
<213> ORGANISM: Artificial sequence.
<220> FEATURE:
<223> OTHER INFORMATION: Synthetic nucleic acid.

<400> SEQUENCE: 16
ttctaatacg actcactata ggg                                               23

<210> SEQ ID NO 17
<211> LENGTH: 18
<212> TYPE: DNA
<213> ORGANISM: Artificial sequence.
<220> FEATURE:
<223> OTHER INFORMATION: Synthetic nucleic acid.

<400> SEQUENCE: 17
aacaaagctg tttcgtcc                                                     18

<210> SEQ ID NO 18
<211> LENGTH: 148
<212> TYPE: DNA
<213> ORGANISM: Artificial sequence.
<220> FEATURE:
<223> OTHER INFORMATION: Synthetic nucleic acid.

<400> SEQUENCE: 18
ttctaatacg actcactata gggggggaaac aaacaaagtt gttttgctgt caccggatgt      60
gctttccggt ctgatgagtc cgttgtccat accagcatcg tcttgatgcc cttggcaggg     120
acgggacgga ggacgaaaca gctttgtt                                        148

<210> SEQ ID NO 19
<211> LENGTH: 148
<212> TYPE: DNA
<213> ORGANISM: Artificial sequence.
<220> FEATURE:
<223> OTHER INFORMATION: Synthetic nucleic acid.

<400> SEQUENCE: 19
ttctaatacg actcactata gggggggaaac aaacaaagtt gttttgctgt caccggaatc      60

```
aaggtccggt ctgatgagtc cgttgtccat accagcatcg tcttgatgcc cttggcaggg    120
acgggacgga ggacgaaaca gctttgtt                                      148
```

<210> SEQ ID NO 20
<211> LENGTH: 148
<212> TYPE: DNA
<213> ORGANISM: Artificial sequence.
<220> FEATURE:
<223> OTHER INFORMATION: Synthetic nucleic acid.

<400> SEQUENCE: 20

```
ttctaatacg actcactata gggggggaaac aaacaaagtt gttttgctgt caccggatgt    60
gctttccggt ctgatgagtc cgttgagtat accagcatcg tcttgatgcc cttggcagac   120
tgtatacgga ggacgaaaca gctttgtt                                      148
```

<210> SEQ ID NO 21
<211> LENGTH: 124
<212> TYPE: DNA
<213> ORGANISM: Artificial sequence.
<220> FEATURE:
<223> OTHER INFORMATION: Synthetic nucleic acid.

<400> SEQUENCE: 21

```
ttctaatacg actcactata gggaaacaaa caaagttgtt ttgctgtcac cggaatacca    60
gcatcgtctt gatgcccttg gaagtccggt ctgatgagtc caaaaaggac gaaacagctt   120
tgtt                                                                124
```

<210> SEQ ID NO 22
<211> LENGTH: 75
<212> TYPE: RNA
<213> ORGANISM: Artificial sequence.
<220> FEATURE:
<223> OTHER INFORMATION: Synthetic nucleic acid.
<220> FEATURE:
<221> NAME/KEY: misc_feature
<222> LOCATION: (13)..(16)
<223> OTHER INFORMATION: This stretch of nucleotides can be any
      nucleotide.
<220> FEATURE:
<221> NAME/KEY: misc_feature
<222> LOCATION: (61)..(61)
<223> OTHER INFORMATION: This nucleotide can be C or A.

<400> SEQUENCE: 22

```
gcugucaccg gannnnuccg gucugaugag uccauaccag caucgucuug augcccuugg    60
magggacgaa acagc                                                    75
```

<210> SEQ ID NO 23
<211> LENGTH: 49
<212> TYPE: RNA
<213> ORGANISM: Artificial sequence.
<220> FEATURE:
<223> OTHER INFORMATION: Synthetic nucleic acid.
<220> FEATURE:
<221> NAME/KEY: misc_feature
<222> LOCATION: (13)..(16)
<223> OTHER INFORMATION: This stretch of nucleotides can be any
      nucleotide.
<220> FEATURE:
<221> NAME/KEY: misc_feature
<222> LOCATION: (34)..(37)
<223> OTHER INFORMATION: This stretch of nucleotides can be any
      nucleotide.

<400> SEQUENCE: 23

```
gcugucaccg gannnnuccg gucugaugag uccnnnngga cgaaacagc        49
```

<210> SEQ ID NO 24
<211> LENGTH: 92
<212> TYPE: RNA
<213> ORGANISM: Artificial sequence.
<220> FEATURE:
<223> OTHER INFORMATION: Synthetic nucleic acid.
<220> FEATURE:
<221> NAME/KEY: misc_feature
<222> LOCATION: (13)..(16)
<223> OTHER INFORMATION: This stretch of nucleotides can be any
      nucleotide.

<400> SEQUENCE: 24

```
gcugucaccg gannnnuccg gucugaugag uccaaaacau accagauuuc gaucuggaga    60
ggugaagaau ucgaccaccu ggacgaaaca gc                                 92
```

<210> SEQ ID NO 25
<211> LENGTH: 64
<212> TYPE: RNA
<213> ORGANISM: Artificial sequence.
<220> FEATURE:
<223> OTHER INFORMATION: Synthetic nucleic acid.
<220> FEATURE:
<221> NAME/KEY: misc_feature
<222> LOCATION: (13)..(16)
<223> OTHER INFORMATION: This stretch of nucleotides can be any
      nucleotide.

<400> SEQUENCE: 25

```
gcugucaccg gannnnuccg gucugaugag uccgcuuguc cuuuaauggu ccggacgaaa    60
cagc                                                                64
```

<210> SEQ ID NO 26
<211> LENGTH: 75
<212> TYPE: RNA
<213> ORGANISM: Artificial sequence.
<220> FEATURE:
<223> OTHER INFORMATION: Synthetic nucleic acid.
<220> FEATURE:
<221> NAME/KEY: misc_feature
<222> LOCATION: (60)..(63)
<223> OTHER INFORMATION: This stretch of nucleotides can be any
      nucleotide.

<400> SEQUENCE: 26

```
gcugucaccg gaauaccagc aucgucuuga ugcccuuggc aguccggucu gaugaguccn    60
nnnggacgaa acagc                                                    75
```

<210> SEQ ID NO 27
<211> LENGTH: 93
<212> TYPE: RNA
<213> ORGANISM: Artificial sequence.
<220> FEATURE:
<223> OTHER INFORMATION: Synthetic nucleic acid.
<220> FEATURE:
<221> NAME/KEY: misc_feature
<222> LOCATION: (57)..(60)
<223> OTHER INFORMATION: This stretch of nucleotides can be any
      nucleotide.
<220> FEATURE:
<221> NAME/KEY: misc_feature
<222> LOCATION: (78)..(81)
<223> OTHER INFORMATION: This stretch of nucleotides can be any
      nucleotide.

<400> SEQUENCE: 27

```
ggugauacca gcaucgucuu gaugcccuug gcagcaccaa aaaagcuguc accggannnn        60
uccggucuga ugaguccnnn nggacgaaac agc                                    93

<210> SEQ ID NO 28
<211> LENGTH: 75
<212> TYPE: RNA
<213> ORGANISM: Artificial sequence.
<220> FEATURE:
<223> OTHER INFORMATION: Synthetic nucleic acid.
<220> FEATURE:
<221> NAME/KEY: misc_feature
<222> LOCATION: (60)..(63)
<223> OTHER INFORMATION: This stretch of nucleotides can be any
      nucleotide.

<400> SEQUENCE: 28
gcugucguug ggauaccagc aucgucuuga ugcccuuggc aguccggucu gaugaguccn        60
nnnggacgaa acagc                                                        75
```